United States Patent [19]

Baker et al.

[11] Patent Number: 5,268,378
[45] Date of Patent: Dec. 7, 1993

[54] DIOXO-TETRAHYDROQUINOLINE DERIVATIVES

[75] Inventors: Raymond Baker, Much Hadham; Paul D. Leeson, Cambridge; Michael Rowley, Harlow; Graeme I. Sevenson, Sawbridgeworth, all of England

[73] Assignee: Merck Sharp & Dohme, Limited, Hoddesdon, England

[21] Appl. No.: 825,442

[22] Filed: Jan. 22, 1992

Related U.S. Application Data

[63] Continuation of Ser. No. 705,976, May 28, 1991, abandoned.

[30] Foreign Application Priority Data

May 31, 1990 [GB] United Kingdom ............... 9012165
Apr. 18, 1991 [GB] United Kingdom ............... 9108356

[51] Int. Cl.$^5$ ........................................ C07D 215/58
[52] U.S. Cl. ................................... 514/312; 514/253; 514/235.2; 514/266; 544/128; 544/238; 544/336; 544/405; 544/90; 546/139; 546/156; 546/155
[58] Field of Search ................. 514/312; 546/155

[56] References Cited

U.S. PATENT DOCUMENTS

| 3,574,216 | 8/1971 | Bell | 546/155 |
| 5,175,151 | 12/1992 | Afonso et al. | 546/155 |
| 5,179,003 | 1/1983 | Afonso et al. | 546/155 |
| 5,179,107 | 1/1993 | Afonso et al. | 546/155 |

FOREIGN PATENT DOCUMENTS

| 0386839 | 2/1990 | European Pat. Off. | |
| 0016878 | 1/1984 | Japan | 546/155 |
| 0152966 | 6/1990 | Japan | 546/155 |
| 90-15052 | 12/1990 | PCT Int'l Appl. | 546/155 |

Primary Examiner—Donald G. Daus
Attorney, Agent, or Firm—Robert J. North; William H. Nicholson; Joseph F. DiPrima

[57] ABSTRACT

A class of 2,4-dioxo-1,2,3,4-tetrahydroquinoline derivatives, substituted at the 3-position by a range of carbonyl-containing substituents or by a five- or six-membered heteroaromatic moiety, are selective non-competitive antagonists of NMDA receptors and/or are antagonists of AMPA receptors, and are therefore of utility in the treatment of conditions, such as neurodegenerative disorders, convulsions or schizophrenia, which require the administration of an NMDA and/or AMPA antagonist.

10 Claims, No Drawings

DIOXO-TETRAHYDROQUINOLINE DERIVATIVES

This is a continuation of application Ser. No. 705,976, filed May 28, 1991, now abandoned.

This invention relates to a class of 3-substituted 2,4-dioxo-1,2,3,4-tetrahydroquinolines which are selective non-competitive antagonists of N-methyl-D-aspartate (NMDA) receptors. More particularly, the class of compounds provided by the present invention are ligands for the strychnine-insensitive glycine modulatory site of the NMDA receptor and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by exogenous and endogenous NMDA receptor agonists and neurotoxins, including environmental neurotoxins.

By virtue of their NMDA receptor antagonist properties, the compounds according to the present invention are also useful as anticonvulsant agents, as well as being of value in the prevention or reduction of dependence on dependence-inducing agents such as narcotics.

NMDA receptor antagonists have recently been shown to possess analgesic (see, for example, Dickenson and Aydar, *Neuroscience Lett.*, 1991, 121, 263; Murray et al., *Pain*, 1991, 44, 179; and Woolf and Thompson, *Pain*, 1991, 44, 293), antidepressant (see, for example, Trullas and Skolnick, *Eur. J. Pharmacol.*, 1990, 185, 1) and anxiolytic (see, for example, Kehne et al., 1991, 193, 283) effects, and the compounds of the present invention may accordingly be useful in the management of pain, depression and anxiety.

The association of NMDA receptor antagonists with regulation of the nigrostriatal dopaminergic system has recently been reported (see, for example, Werling et al., *J. Pharmacol. Exp. Ther.*, 1990, 255, 40; Graham et al., *Life Sciences*, 1990, 47, PL-41; and Turski et al., *Nature* (London), 1991, 349, 414). This suggests that the compounds of the present invention may thus be of assistance in the prevention and/or treatment of disorders of the dopaminergic system such as schizophrenia and Parkinson's disease.

Recent reports in the literature have also suggested a link between the neurotoxicity of certain viruses and the deleterious effects of these viruses on neurotransmission via excitatory amino acid receptors. By virtue of their activity as antagonists of NMDA receptors, therefore, the compounds of the present invention may be effective in controlling the manifestations of neuroviral diseases such as measles, rabies, tetanus (cf. Bagetta et al., *Br. J. Pharmacol.*, 1990, 101, 776) and AIDS (cf. Lipton et al., *Society for Neuroscience Abstracts*, 1990, 16, 128.11).

NMDA antagonists have, moreover, been shown to have an effect on the neuroendocrine system (see, for example, van den Pol et al., *Science*, 1990, 250, 1276; and Urbanski, *Endocrinology*, 1990, 127, 2223), and the compounds of this invention may therefore also be effective in the control of seasonal breeding in mammals.

In addition, certain compounds of the invention are antagonists of 2-amino-3-hydroxy-5-methyl-4-isoxazolepropionic acid (AMPA) receptors, also known as quisqualate receptors. An excitatory amino acid projection from the prefrontal cortex to the nucleus accumbens (a particular region of the forebrain possessing dopamine-sensitive neurones) is well known to exist (see, for example, *J. Neurochem.*, 1985, 45, 477). It is also well known that dopaminergic transmission in the striatum is modulated by glutamate (see, for example, *Neurochem. Int.*, 1983, 5, 479), as also is the hyperactivity associated with presynaptic stimulation of the dopamine system by AMPA in the nucleus accumbens (cf. *Life Sci.*, 1981, 28, 1597). Compounds which are antagonists of AMPA receptors are therefore of value as neuroleptic agents.

The use of 3-alkoxycarbonyl-substituted 2,4-dioxo-1,2,3,4-tetrahydroquinoline derivatives which are unsubstituted on the benzo moiety, as intermediates in the synthesis of various 2,4-dioxo-1,2,3,4-tetrahydroquinoline-3-carboxamide derivatives, is described in JP-A-43-23948. The latter compounds are stated to be antibacterial agents.

Various classes of 2,4-dioxo-1,2,3,4-tetrahydroquinolines, substituted at the 3-position by a cyano, carboxy or ester group, are described in BE-A-851866, DE-A-2806879, EP-A-0000153, corresponding to U.S. Pat. Nos. 4,187,309 and 4,281,131 U.S. Pat. Nos. 4,119,720 and 4,221,797. These compounds are stated to be antiallergic agents. The class of 3-cyano-substituted 2,4-dioxo-1,2,3,4-tetrahydroquinolines described in DE-A-3620856 corresponding to U.S. Pat. No. 4,927,935 are stated to be dyestuff intermediates. U.S. Pat. No. 4,362,876 describes a process for preparing further 3-cyano-substituted 2,4-dioxo-1,2,3,4-tetrahydroquinoline derivatives. A still further class of 2,4-dioxo-1,2,3,4-tetrahydroquinolines, which are substituted on the benzo moiety by inter alia a cycloaliphatic group, is described in BE-A-814843 corresponding to U.S. Pat. No. 3,960,868. This class of compounds is alleged to have analgesic, antinociceptive, anti-inflammatory, antimicrobial, antibacterial, fungistatic, antiviral, coccidiostatic and antiallergic properties, with low toxicity.

Additional classes of 2,4-dioxo-1,2,3,4-tetrahydroquinoline derivatives are described in *Monatsh. Chem.*, 1978, 109, 1075, *Chem. Pharm. Bull.*, 1959, 7, 547, *J. Org. Chem.*, 1964, 29, 2598, *J. Org. Chem.*, 1969, 34, 2183, *Eur. J. Med. Chem.*, 1981, 16, 251, *Synthesis*, 1979, 590, *Yakugaku Zasshi*, 1970, 90, 818, and *J. Chem. Soc.*, 1950, 1678.

A class of 2,4-dioxo-1,2,3,4-tetrahydroquinoline-3-carboxamide derivatives is described in EP-A-0059698 corresponding to U.S. Pat. No. 4,547,511. These compounds are alleged to demonstrate an enhancing effect upon cell-mediated immunity, whilst also having a low toxicity, resulting in a favourable therapeutic index. EP-A-0059698 also discloses N-substituted 3-carboxy-2,4-dioxo-1,2,3,4-tetrahydroquinolines, and reactive derivatives thereof, as intermediates.

JP-A-59-16878 describes a process for producing 3-acetyl-2,4-dioxo-1,2,3,4-tetrahydroquinoline derivatives carrying a range of substituents on the benzo moiety. The compounds prepared by this process are stated to be useful intermediates in the production of therapeutic agents for allergic asthma.

A class of 2,4-dioxo-1,2,3,4-tetrahydroquinolines bearing an optionally substituted benzoyl moiety in the 3-position is described in EP-A-0101330. These compounds are stated to possess anti-inflammatory, antiallergic, antiasthmatic, antitussive and expectorant properties.

None of the aforementioned documents, however, discloses the particular class of 3-substituted 2,4-dioxo-1,2,3,4-tetrahydroquinolines provided by the present invention. Moreover, in none of those documents is there any suggestion that the compounds described therein would be of assistance in solving the problem of providing an effective agent for the treatment and/or prevention of conditions requiring the administration of an antagonist of NMDA and/or AMPA receptors.

The present invention accordingly provides the use of a compound of formula IA or a pharmaceutically acceptable salt thereof or a prodrug thereof:

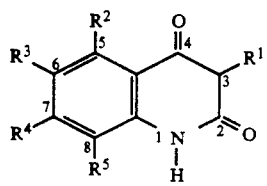

(IA)

wherein
$R^1$ is a group of part formula (i) or (ii):

  (i)

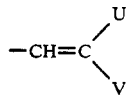  (ii)

wherein
U and V independently represent cyano, carboxy, —$COR^6$, —$CO_2R^6$, —$CO.SR^6$, —CONHOH or —$CONHNH_2$;
n is zero or 1, preferably zero;
T represents cyano, carboxy, —$COR^6$, —$CO_2R^6$, —$CO.SR^6$, —CONHOH, —$CONHNH_2$ or a group of formula

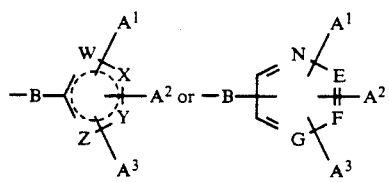

in which the broken circle represents two non-adjacent double bonds in any position in the five-membered ring;
B represents a bond or a carbonyl group (C=O);
W, X, Y and Z independently represent oxygen, sulphur, nitrogen or carbon, provided that no more than one of W, X, Y and Z represents oxygen or sulphur, at least one of W, X, Y and Z represents carbon and at least one of W, X, Y and Z is other than carbon;
one of E, F and G represents nitrogen or carbon and the remainder represent carbon;
$A^1$, $A^2$ and $A^3$ represent one, two or three substituents not exceeding the maximum number permissible by the disposition of heteroatoms in the five- or six-membered ring, which substituents are independently selected from hydrogen, hydrocarbon, halogen, cyano, trifluoromethyl, nitro, —$OR^a$, —$SR^a$, —$SOR^a$, —$SO_2R^a$, —$SO_2NR^aR^b$, —$NR^aR^b$, —N-

$R^aCOR^b$, —$NR^aCO_2R^b$, —$COR^a$, —$CO_2R^a$ or —$CONR^aR^b$; or $A^1$ and $A^2$ or $A^2$ and $A^3$ together represent the residue of an aromatic or heteroaromatic ring;
$R^2$, $R^3$, $R^4$ and $R^5$ independently represent hydrogen, hydrocarbon, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; or $R^2$ and $R^3$, $R^3$ and $R^4$ or $R^4$ and $R^5$ together represent the residue of an aromatic or heteroaromatic ring;
$R^6$ represents hydrocarbon; and
$R^a$ and $R^b$ independently represent hydrogen or hydrocarbon;
for the manufacture of a medicament for the treatment and/or prevention of conditions, in particular neurodegenerative disorders, which require the administration of a selective non-competitive antagonist of NMDA receptors.

The present invention further provides the use of a compound of formula IA as defined above or a pharmaceutically acceptable salt thereof or a prodrug thereof for the manufacture of a medicament for the treatment and/or prevention of conditions, such as schizophrenia, which require the administration of an antagonist of AMPA receptors.

The compound of formula IA will in general exist in equilibrium with its other tautomeric forms, including those structures of formulae A to D:

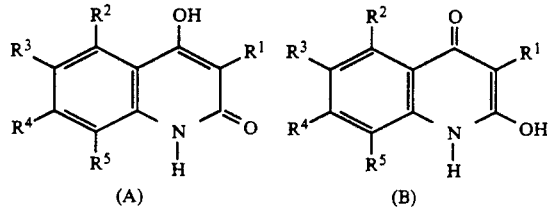

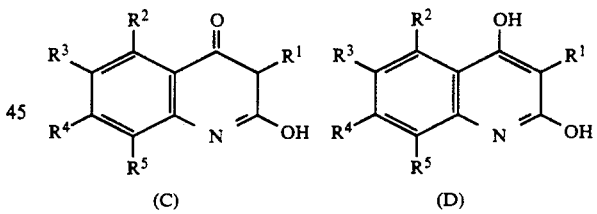

wherein $R^1$ to $R^5$ are as defined with reference to formula IA above. Indeed, in the prior art references cited above, the compounds disclosed therein are variously designated by reference to one or other of these tautomeric forms. It is to be understood that all tautomeric forms of the compounds of formula IA, as well as all possible mixtures thereof, are included within the scope of the present invention.

The term "hydrocarbon" as used herein includes straight-chained, branched and cyclic groups, including heterocyclic groups, containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, $C_{3-7}$ heterocycloalkyl, $C_{3-7}$ heterocycloalkyl($C_{1-6}$)alkyl, heteroaryl, heteroaryl($C_{1-6}$)alkyl and heteroaryl($C_{2-6}$)alkenyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

Particular aryl($C_{1-6}$)alkyl groups include benzyl, phenethyl, phenylpropyl and phenylbutyl.

A particular aryl($C_{2-6}$)alkenyl group is phenylallyl.

A particular aryl($C_{2-6}$)alkynyl group is phenylpropargyl.

Suitable heterocycloalkyl groups include piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, thienyl, benzthienyl, pyrrolyl, indolyl, imidazolyl, oxadiazolyl and thiadiazolyl groups. Particular heteroaryl groups are pyridyl, furyl, benzofuryl, thienyl, benzthienyl, pyrrolyl, indolyl and oxadiazolyl.

Particular heteroaryl($C_{1-6}$)alkyl groups include indolylethyl, indolylpropyl and thienylethyl.

A particular heteroaryl($C_{2-6}$)alkenyl group is thienylvinyl.

The hydrocarbon group may in turn be optionally substituted by one or more groups selected from $C_{1-6}$ alkyl, adamantyl, phenyl, halogen, $C_{1-6}$ haloalkyl, trifluoromethyl, hydroxy, $C_{1-6}$ alkoxy, $C_{1-6}$ alkoxy($C_{1-6}$)alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, optionally substituted arylcarbonyloxy, $C_{2-6}$ alkylcarbonyl, optionally substituted arylcarbonyl, $C_{1-6}$ alkylthio, $C_{1-6}$ alkylsulphinyl, $C_{1-6}$ alkylsulphonyl, arylthio, amino, mono- or di($C_{1-6}$)alkylamino, $C_{2-6}$ alkylcarbonylamino, $C_{2-6}$ alkoxycarbonylamino and $C_{2-6}$ alkoxycarbonylamino($C_{1-6}$)alkyl.

The term "halogen" as used herein includes fluorine, chlorine, bromine and iodine, especially chlorine.

The five-membered heteroaromatic ring containing the ring atoms W to Z may be, for example, a furan, thiophene, pyrrole, oxazole, thiazole, isoxazole, isothiazole, oxadiazole or thiadiazole ring, in particular a furan, thiophene, pyrrole, 1,2,4-oxadiazole, 1,3,4-oxadiazole, 1,2,4-thiadiazole or 1,3,4-thiadiazole ring. Preferably the ring is a furan, thiophene, pyrrole, 1,2,4-oxadiazole or 1,2,4-thiadiazole ring.

The six-membered heteroaromatic ring containing the ring atoms E, F and G is a pyridine, pyrazine, pyrimidine or pyridazine ring, preferably pyridine or pyrazine. In the case of a pyridine ring, E, F and G each represents carbon. In the case of a pyrazine ring, for example, G represents nitrogen, and E and F each represents carbon.

The number of substituents $A^1$, $A^2$ and/or $A^3$ present on the five- or six-membered heteroaromatic ring containing the ring atoms W to Z or E to G respectively is one, two or three depending upon the disposition of heteroatoms in the heteroaromatic ring concerned. Thus where, for example, the five-membered heteroaromatic ring is an oxadiazole or thiadiazole ring, only one substituent will be permitted; where, for example, the five-membered heteroaromatic ring is an oxazole or thiazole ring, one or two substituents will be permitted; and where, for example, the five-membered heteroaromatic ring is a furan, thiophene or pyrrole ring, one, two or three substituents will be permitted. Where the heteroaromatic ring is a six-membered ring containing the ring atoms E, F and G it will be appreciated that one, two or three substituents $A^1$, $A^2$ and/or $A^3$ will be permitted.

Suitable values for the groups $A^1$, $A^2$ and/or $A^3$ include hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, optionally substituted aryl, optionally substituted aryl($C_{1-6}$)alkyl, halogen, cyano, trifluoromethyl, nitro, $C_{1-6}$ alkoxy, $C_{2-6}$ alkenyloxy, $C_{1-6}$ alkylthio, $C_{2-6}$ alkenylthio, —$COR^a$ or —$NR^aR^b$, in which $R^a$ and $R^b$ are as defined above.

When T, U or V represents a group of formula —$COR^6$, —$CO_2R^6$ or —$CO.SR^6$, the substituent $R^6$ suitably represents $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl or heteroaryl($C_{2-6}$)alkenyl, any of which groups may be optionally substituted.

The benzo moiety of the tetrahydroquinoline ring system shown in formula IA above preferably contains at least one non-hydrogen substituent. Particular substituents include halogen, cyano, trifluoromethyl, nitro, hydroxy, amino, carboxy, $C_{1-6}$ alkyl, $C_{1-6}$ alkoxy, $C_{1-6}$ alkylthio and $C_{2-6}$ alkoxycarbonyl. Suitably, $R^5$ represents hydrogen and $R^2$, $R^3$ and $R^4$ independently represent hydrogen, halogen, nitro, amino or $C_{1-6}$ alkyl, provided that at least one of $R^2$, $R^3$ and $R^4$ is other than hydrogen. Preferably, $R^3$ and $R^5$ each represents hydrogen and $R^2$ and $R^4$ independently represent hydrogen, nitro, amino, methyl or halogen, especially chlorine, provided that at least one of $R^2$ and $R^4$ is other than hydrogen. In a preferred embodiment, $R^4$ represents chlorine.

Where $R^2$ and $R^3$, $R^3$ and $R^4$, $R^4$ and $R^5$, $A^1$ and $A^2$ or $A^2$ and $A^3$ represent the residue of an aromatic or heteroaromatic ring, this is suitably an optionally substituted benzene, pyridine, thiophene, thiazole or thiadiazole ring. As optional substituents on the aromatic or heteroaromatic ring may be mentioned nitro, and $C_{1-6}$ alkoxy such as methoxy.

Certain compounds falling within the definition of formula IA above are novel. Accordingly, in a further aspect the present invention provides a compound of formula IB or a salt or prodrug thereof:

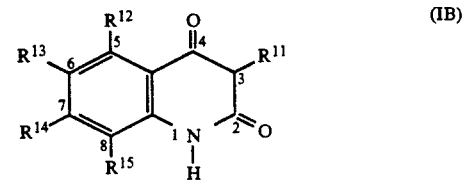

(IB)

wherein $R^{11}$ is a group of part formula (i) or (ii):

$$-(CH=CH)_n-T \quad \text{(i)}$$

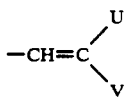

$$-CH=C\begin{matrix}U\\V\end{matrix} \quad \text{(ii)}$$

wherein

U and V independently represent cyano, carboxy, —COR$^6$, —CO$_2$R$^6$, —CO.SR$^6$, —CONHOH or —CONHNH$_2$;

n is zero or 1, preferably zero;

T represents cyano, carboxy, —COR$^6$, —CO$_2$R$^6$, —CO.SR$^6$, —CONHOH, —CONHNH$_2$ or a group of formula

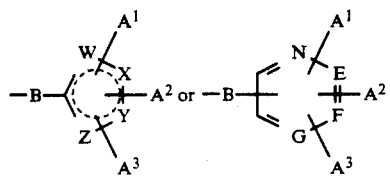

in which the broken circle represents two non-adjacent double bonds in any position in the five-membered ring;

B represents a bond or a carbonyl group (C=O);

W, X, Y and Z independently represent oxygen, sulphur, nitrogen or carbon, provided that no more than one of W, X, Y and Z represents oxygen or sulphur, at least one of W, X, Y and Z represents carbon and at least one of W, X, Y and Z is other than carbon;

one of E, F and G represents nitrogen or carbon and the remainder represent carbon;

A$^1$, A$^2$ and A$^3$ represent one, two or three substituents not exceeding the maximum number permissible by the disposition of heteroatoms in the five- or six-membered ring, which substituents are independently selected from hydrogen, hydrocarbon, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$; or A$^1$ and A$^2$ or A$^2$ and A$^3$ together represent the residue of an aromatic or heteroaromatic ring;

R$^{12}$, R$^{13}$, R$^{14}$ and R$^{15}$ independently represent hydrogen, hydrocarbon, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$; or R$^{12}$ and R$^{13}$, R$^{13}$ and R$^{14}$ or R$^{14}$ and R$^{15}$ together represent the residue of an aromatic or heteroaromatic ring;

R$^6$ represents hydrocarbon; and

R$^a$ and R$^b$ independently represent hydrogen or hydrocarbon;

provided that:

(a) when two of the substituents R$^{12}$ to R$^{15}$ represent hydrogen and the other two substituents R$^{12}$ to R$^{15}$ independently represent hydrogen, C$_{1-8}$ alkyl, halogen, C$_{1-5}$ alkoxy, nitro, cyano, C$_{1-3}$ haloalkyl, carboxy or C$_{2-4}$ alkoxycarbonyl, then R$^{11}$ does not represent a benzoyl group optionally mono-, di- or trisubstituted by C$_{1-8}$ alkyl, halogen, C$_{1-5}$ alkoxy, nitro, cyano, C$_{1-3}$ haloalkyl, carboxy or C$_{2-4}$ alkoxycarbonyl;

(b) when R$^{12}$ to R$^{15}$ independently represent hydrogen, C$_{1-5}$ alkyl, C$_{1-5}$ alkoxy, benzyloxy, C$_{2-6}$ alkoxycarbonyl, nitro or halogen, then R$^{11}$ does not represent acetyl;

(c) when one of R$^{12}$ to R$^{15}$ represents hydrogen or methoxy and the remainder represent hydrogen, then R$^{11}$ does not represent —CONHNH$_2$ or —COR$^6$, in which R$^6$ is C$_{2-9}$ alkyl;

(d) when two of the substituents R$^{12}$ to R$^{15}$ represent hydrogen and the other two substituents R$^{12}$ to R$^{15}$ independently represent hydrogen, halogen, C$_{1-4}$ alkyl, C$_{1-4}$ alkoxy, nitro or trifluoromethyl or together represent methylenedioxy, then R$^{11}$ does not represent cyano, carboxy or —CO$_2$R$^6$, in which R$^6$ is C$_{1-9}$ alkyl, C$_{3-6}$ alkenyl or C$_{3-6}$ alkynyl;

(e) when two of the substituents R$^{12}$ to R$^{15}$ represent hydrogen, a third substituent R$^{12}$ to R$^{15}$ represents an optionally substituted C$_{5-8}$ cycloalkyl or cycloalkenyl group or adamantyl, and the remaining substituent R$^{12}$ to R$^{15}$ represents hydrogen, halogen, lower alkyl or lower alkoxy, then R$^{11}$ does not represent carboxy or —COR$^{16}$, in which R$^{16}$ is an etherified hydroxyl group;

(f) when R$^{12}$ to R$^{15}$ each represents hydrogen and R$^{11}$ is a group of part formula (ii) as defined above, then U and V are not simultaneously carboxy, and U is not carboxy or ethoxycarbonyl when V is cyano; and (g) when R$^{12}$ to R$^{15}$ each represents hydrogen, then R$^{11}$ does not represent unsubstituted 2-pyridyl, 3-pyridyl, 2-furyl or 2-benzothiazolyl.

Subject to the above provisos, the substituents R$^{11}$ to R$^{15}$ in the compounds of formula IB correspond to the substituents R$^1$ to R$^5$ respectively as defined with reference to the compounds of formula IA.

Representative values of R$^{11}$ include cyano, carboxy, cyclopropylcarbonyl, benzylcarbonyl, thienylvinylcarbonyl, methoxycarbonyl, ethoxycarbonyl, phenylthioethoxycarbonyl, propoxycarbonyl, allyloxycarbonyl, hydroxyphenyl-ethoxycarbonyl, bis(methoxymethoxy)-phenyl-ethoxycarbonyl, (t-butoxycarbonylaminomethyl)phenyl-ethoxycarbonyl, hydroxyphenyl-propoxycarbonyl, hydroxyphenylbutoxycarbonyl, methoxyphenyl-propenyloxycarbonyl, hydroxyphenylpropynyloxycarbonyl, methoxyphenyl-propynyloxycarbonyl, thienyl-ethoxycarbonyl, indolylethoxycarbonyl, methoxyindolyl-ethoxycarbonyl, indolylpropoxycarbonyl, phenethylthio-carbonyl, hydroxyaminocarbonyl, hydrazinocarbonyl, furyl, methylfuryl, ethylfuryl, isopropylfuryl, phenylfuryl, benzofuryl, thienyl, methylthienyl, benzylthienyl, benzothienyl, N-methylpyrrolyl, benzoyl-(N-methyl)pyrrolyl, methyloxadiazolyl, furoyl, methylfuroyl, dimethylfuroyl, benzofuroyl, nitro-benzofuroyl, thienoyl, methylthienoyl, bromothienoyl, dimethylthienoyl, benzothienoyl, N-methylpyrrolylcarbonyl, N-methylindolylcarbonyl, pyridyl and ethoxycarbonylethenyl.

For use in medicine, the salts of the compounds of formula IB will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formulae IA and IB above include alkali metal salts, e.g. sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid.

The present invention includes within its scope prodrugs of the compounds of formulae IA and IB above. In general, such prodrugs will be functional derivatives of the compounds of formulae IA and IB which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

One sub-class of compounds according to the invention is represented by the compounds of formula IIA, and salts and prodrugs thereof:

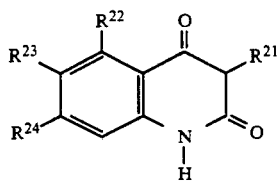

wherein
$R^{21}$ represents —$COR^{26}$ or —$CO_2R^{26}$;
$R^{22}$, $R^{23}$ and $R^{24}$ independently represent hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl, provided that at least one of $R^{22}$, $R^{23}$ and $R^{24}$ is other than hydrogen; and
$R^{26}$ represents $C_{3-7}$ cycloalkyl, aryl($C_{1-6}$)alkyl, aryl($C_{2-6}$)alkenyl, aryl($C_{2-6}$)alkynyl, heteroaryl($C_{1-6}$)alkyl or heteroaryl($C_{2-6}$)alkenyl, any of which groups may be optionally substituted.

Examples of optional substituents on the group $R^{26}$ suitably include hydroxy, $C_{1-6}$ alkoxy, $C_{1-6}$ alkoxy($C_{1-6}$)alkoxy and $C_{2-6}$ alkoxycarbonylamino($C_{1-6}$)alkyl, especially hydroxy, methoxy, methoxymethoxy and t-butoxycarbonylaminomethyl.

Particular values of $R^{26}$ with respect to formula IIA include cyclopropyl, benzyl, phenethyl, hydroxyphenethyl, bis(methoxymethoxy)phenethyl, (t-butoxycarbonylaminomethyl)phenethyl, phenylpropyl, hydroxyphenylpropyl, phenylbutyl, hydroxyphenylbutyl, phenylallyl, methoxyphenylallyl, phenylpropargyl, hydroxyphenylpropargyl, methoxyphenylpropargyl, indolylethyl, methoxyindolylethyl, indolylpropyl, thienylethyl and thienylvinyl. A preferred group $R^{26}$ is cyclopropyl.

Suitably, $R^{22}$, $R^{23}$ and $R^{24}$ are independently selected from hydrogen, halogen, nitro, amino and $C_{1-6}$ alkyl, provided that at least one of $R^{22}$, $R^{23}$ and $R^{24}$ is other than hydrogen. Preferably $R^{23}$ represents hydrogen, one of $R^{22}$ and $R^{24}$ represents halogen or nitro, and the other of $R^{22}$ and $R^{24}$ represents hydrogen, halogen or nitro. In a particular embodiment, $R^{22}$ and $R^{23}$ each represents hydrogen and $R^{24}$ represents halogen, especially chlorine.

Another sub-class of compounds according to the invention is represented by the compounds of formula IIB, and salts and prodrugs thereof:

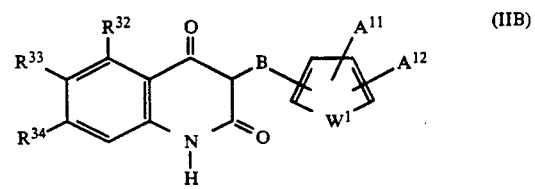

wherein
$W^1$ represents oxygen, sulphur or N—$A^{13}$;
$A^{11}$ and $A^{12}$ independently represent hydrogen, halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, $C_{1-6}$ alkoxy, $C_{2-6}$ alkenyloxy, $C_{1-6}$ alkylthio, $C_{2-6}$ alkenylthio, $C_{2-6}$ alkylcarbonyl, arylcarbonyl or $C_{2-6}$ alkoxycarbonyl; or $A^{11}$ and $A^{12}$ together represent the residue of an optionally substituted aromatic or heteroaromatic ring;
$A^{13}$ represents hydrogen, $C_{1-6}$ alkyl or aryl($C_{1-6}$)alkyl;
B represents a bond or a carbonyl group (C=O); and
$R^{32}$, $R^{33}$ and $R^{34}$ independently represent hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl, provided that at least one of $R^{32}$, $R^{33}$ and $R^{34}$ is other than hydrogen.

Examples of suitable values for the groups $A^{11}$ and $A^{12}$ include hydrogen, halogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, $C_{1-6}$ alkoxy, $C_{2-6}$ alkenyloxy, $C_{1-6}$ alkylthio, $C_{2-6}$ alkenylthio and arylcarbonyl. Particular values of $A^{11}$ and $A^{12}$ include hydrogen, bromo, methyl, ethyl, isopropyl, vinyl, allyl, cyclopropyl, cyclopropylmethyl, phenyl, benzyl, allyloxy, allylthio and benzoyl.

Where $A^{11}$ and $A^{12}$ together represent the residue of an optionally substituted aromatic or heteroaromatic ring, this is preferably an optionally substituted benzene ring. Examples of optional substituents on the aromatic or heteroaromatic ring suitably include nitro, and $C_{1-6}$ alkoxy such as methoxy.

Suitably, $A^{13}$ represents hydrogen or methyl, preferably methyl.

Suitably, $R^{32}$, $R^{33}$ and $R^{34}$ are independently selected from hydrogen, halogen, nitro, amino and $C_{1-6}$ alkyl, provided that at least one of $R^{32}$, $R^{33}$ and $R^{34}$ is other than hydrogen. Preferably $R^{33}$ represents hydrogen, one of $R^{32}$ and $R^{34}$ represents halogen or nitro, and the other of $R^{32}$ and $R^{34}$ represents hydrogen, halogen or nitro. In a particular embodiment, $R^{32}$ and $R^{33}$ each represents hydrogen and $R^{34}$ represents halogen, especially chlorine.

A further sub-class of compounds according to the invention is represented by the compounds of formula IIC, and salts and prodrugs thereof:

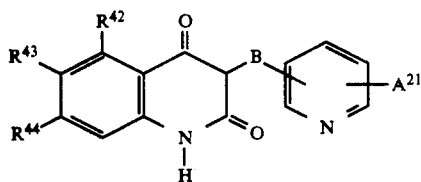
(IIC)

wherein
A$^{21}$ represents hydrogen, halogen, cyano, trifluoromethyl, nitro, hydroxy, amino, carboxy, C$_{1-6}$ alkyl, C$_{1-6}$ alkoxy, C$_{1-6}$ alkylthio, C$_{2-6}$ alkylcarbonyl, arylcarbonyl or C$_{2-6}$ alkoxycarbonyl;
B represents a bond or a carbonyl group (C=O); and
R$^{42}$, R$^{43}$ and R$^{44}$ independently represent hydrogen, halogen, cyano, trifluoromethyl, nitro, hydroxy, amino, carboxy, C$_{1-6}$ alkyl, C$_{1-6}$ alkoxy, C$_{1-6}$ alkylthio or C$_{2-6}$ alkoxycarbonyl, provided that at least one of R$^{42}$, R$^{43}$ and R$^{44}$ is other than hydrogen.

Examples of suitable values for the group A$^{21}$ include hydrogen, halogen, C$_{1-6}$ alkyl and arylcarbonyl. Preferably, A$^{21}$ is hydrogen.

Suitably, R$^{42}$, R$^{43}$ and R$^{44}$ are independently selected from hydrogen, halogen, nitro, amino and C$_{1-6}$ alkyl, provided that at least one of R$^{42}$, R$^{43}$ and R$^{44}$ is other than hydrogen. Preferably R$^{43}$ represents hydrogen, one of R$^{42}$ and R$^{44}$ represents halogen or nitro, and the other of R$^{42}$ and R$^{44}$ represents hydrogen, halogen or nitro. In a particular embodiment, R$^{42}$ and R$^{43}$ each represents hydrogen and R$^{44}$ represents halogen, especially chlorine.

Specific compounds within the scope of the present invention include:
3-benzyloxycarbonyl-7-chloro-2,4-dioxo-1,2,3,4-tetrahydroquinoline;
7-chloro-2,4-dioxo-3-(2-phenylethoxy)carbonyl-1,2,3,4-tetrahydroquinoline;
7-chloro-2,4-dioxo-3-(3-phenylpropoxy)carbonyl-1,2,3,4-tetrahydroquinoline;
7-chloro-2,4-dioxo-3-[2-(3-hydroxyphenyl)ethoxy]carbonyl-1,2,3,4-tetrahydroquinoline;
7-chloro-2,4-dioxo-3-[3-(4-hydroxyphenyl)propoxy]carbonyl-1,2,3,4-tetrahydroquinoline;
7-chloro-2,4-dioxo-3-[2-(2-hydroxyphenyl)ethoxy]carbonyl-1,2,3,4-tetrahydroquinoline;
7-chloro-3-cyclopropylmethoxycarbonyl-2,4-dioxo-1,2,3,4-tetrahydroquinoline;
7-chloro-2,4-dioxo-3-[2-(4-hydroxyphenyl)ethoxy]carbonyl-1,2,3,4-tetrahydroquinoline;
7-chloro-2,4-dioxo-3-(3-hydroxyphenylmethoxy)carbonyl-1,2,3,4-tetrahydroquinoline;
7-chloro-2,4-dioxo-3-(pyrid-2-ylmethoxy)carbonyl-1,2,3,4-tetrahydroquinoline;
2,4-dioxo-3-[-3-(4-hydroxyphenyl)propoxy]carbonyl-7-nitro-1,2,3,4-tetrahydroquinoline;
7-chloro-2,4-dioxo-3-(2-hydroxyethoxy)carbonyl-1,2,3,4-tetrahydroquinoline;
7-chloro-2,4-dioxo-3-(3-thienyl)carbonyl-1,2,3,4-tetrahydroquinoline;
7-chloro-2,4-dioxo-3-(2-furyl)carbonyl-1,2,3,4-tetrahydroquinoline;
7-chloro-2,4-dioxo-3-(2-thienyl)carbonyl-1,2,3,4-tetrahydroquinoline;
7-chloro-3-(2,5-dimethyl-3-furyl)carbonyl-2,4-dioxo-1,2,3,4-tetrahydroquinoline;
7-chloro-2,4-dioxo-3-(5-methyl-2-furyl)carbonyl-1,2,3,4-tetrahydroquinoline;
7-chloro-2,4-dioxo-3-[2-(5-nitrobenzofuryl)carbonyl]-1,2,3,4-tetrahydroquinoline;
3-[2-(benzofuryl)carbonyl]-7-chloro-2,4-dioxo-1,2,3,4-tetrahydroquinoline;
3-[2-(benzo[b]thienyl)carbonyl]-7-chloro-2,4-dioxo-1,2,3,4-tetrahydroquinoline;
3-benzylcarbonyl-7-chloro-2,4-dioxo-1,2,3,4-tetrahydroquinoline;
7-chloro-2,4-dioxo-3-(5-methyl-2-thienyl)carbonyl-1,2,3,4-tetrahydroquinoline;
7-chloro-2,4-dioxo-3-(3-methyl-2-thienyl)carbonyl-1,2,3,4-tetrahydroquinoline;
7-chloro-3-(2,5-dimethyl-3-thienyl)carbonyl-2,4-dioxo-1,2,3,4-tetrahydroquinoline;
7-chloro-2,4-dioxo-3-[2-(3-thienyl)ethenyl]carbonyl-1,2,3,4-tetrahydroquinoline;
3-(5-bromo-2-thienyl)carbonyl-7-chloro-2,4-dioxo-1,2,3,4-tetrahydroquinoline;
7-chloro-2,4-dioxo-3-(1-methylpyrrol-2-yl)carbonyl-1,2,3,4-tetrahydroquinoline;
7-chloro-2,4-dioxo-3-(1-methylpyrrol-3-yl)carbonyl-1,2,3,4-tetrahydroquinoline;
7-chloro-2,4-dioxo-3-(1-methylindol-3-yl)carbonyl-1,2,3,4-tetrahydroquinoline;
7-chloro-3-cyclopropylcarbonyl-2,4-dioxo-1,2,3,4-tetrahydroquinoline;
7-chloro-2,4-dioxo-3-(5-methyl-2-furyl)-1,2,3,4-tetrahydroquinoline;
7-chloro-2,4-dioxo-3-(5-ethyl-2-furyl)-1,2,3,4-tetrahydroquinoline;
7-chloro-2,4-dioxo-3-(1-methylpyrrol-2-yl)-1,2,3,4-tetrahydroquinoline;
7-chloro-2,4-dioxo-3-(2-furyl)-1,2,3,4-tetrahydroquinoline;
3-(4-benzoyl-1-methylpyrrol-2-yl)-7-chloro-2,4-dioxo-1,2,3,4-tetrahydroquinoline;
3-(5-benzoyl-1-methylpyrrol-2-yl)-7-chloro-2,4-dioxo-1,2,3,4-tetrahydroquinoline;
7-chloro-2,4-dioxo-3-[2-(5-methoxyindol-3-yl)ethoxy]carbonyl-1,2,3,4-tetrahydroquinoline;
7-chloro-2,4-dioxo-3-[3-(3-methoxyphenyl)prop-2-ynyloxy]carbonyl-1,2,3,4-tetrahydroquinoline;
7-chloro-2,4-dioxo-3-(3-indol-3-ylpropoxy)carbonyl-1,2,3,4-tetrahydroquinoline;
3-[2-[3,4-bis(methoxymethoxy)phenyl]ethoxy]carbonyl-7-chloro-2,4-dioxo-1,2,3,4-tetrahydroquinoline;
7-chloro-2,4-dioxo-3-[4-(3-hydroxyphenyl)butoxy]carbonyl-1,2,3,4-tetrahydroquinoline;
7-chloro-2,4-dioxo-3-[3-(3-hydroxyphenyl)propoxy]carbonyl-1,2,3,4-tetrahydroquinoline;
7-chloro-2,4-dioxo-3-(2-indol-3-ylethoxy)carbonyl-1,2,3,4-tetrahydroquinoline;
7-chloro-2,4-dioxo-3-[3-(2-hydroxyphenyl)propoxy]carbonyl-1,2,3,4-tetrahydroquinoline;
3-[2-[4-(N-t-butoxycarbonylaminomethyl)phenyl]ethoxy]carbonyl-7-chloro-2,4-dioxo-1,2,3,4-tetrahydroquinoline;
7-chloro-2,4-dioxo-3-[2-(3-thienyl)ethoxy]carbonyl-1,2,3,4-tetrahydroquinoline;
7-chloro-2,4-dioxo-3-[2-(2-thienyl)ethoxy]carbonyl-1,2,3,4-tetrahydroquinoline;
7-chloro-2,4-dioxo-3-[3-(3-hydroxyphenyl)prop-2-ynyloxy]carbonyl-1,2,3,4-tetrahydroquinoline;

7-chloro-2,4-dioxo-3-[3-(3-methoxyphenyl)prop-2-enyloxy]carbonyl-1,2,3,4-tetrahydroquinoline;
7-chloro-2,4-dioxo-3-[2-(phenylthio)ethoxy]carbonyl-1,2,3,4-tetrahydroquinoline;
7-chloro-2,4-dioxo-3-[2-(phenyl)ethylthio]carbonyl-1,2,3,4-tetrahydroquinoline;
7-chloro-2,4-dioxo-3-(2-indol-3-ylethoxy)carbonyl-5-iodo-1,2,3,4-tetrahydroquinoline;
7-chloro-2,4-dioxo-3-(3-methyl-1,2,4-oxadiazo-5-yl)-1,2,3,4-tetrahydroquinoline;
7-chloro-2,4-dioxo-3-[2-(ethoxycarbonyl)ethenyl]-1,2,3,4-tetrahydroquinoline;
7-chloro-2,4-dioxo-1,2,3,4-tetrahydroquinoline-3-hydroxamic acid;
7-chloro-2,4-dioxo-5-iodo-1,2,3,4-tetrahydroquinoline-3-hydroxamic acid;
7-chloro-2,4-dioxo-1,2,3,4-tetrahydroquinoline-3-carboxylic acid hydrazide;
7-chloro-2,4-dioxo-3-(3-thienyl)-1,2,3,4-tetrahydroquinoline;
7-chloro-2,4-dioxo-3-(2-thienyl)-1,2,3,4-tetrahydroquinoline;
7-chloro-2,4-dioxo-3-(2-pyridyl)-1,2,3,4-tetrahydroquinoline;
7-chloro-2,4-dioxo-3-(3-pyridyl)-1,2,3,4-tetrahydroquinoline;
7-chloro-2,4-dioxo-3-(4-pyridyl)-1,2,3,4-tetrahydroquinoline;
3-(2-benzofuryl)-7-chloro-2,4-dioxo-1,2,3,4-tetrahydroquinoline;
3-(3-benzofuryl)-7-chloro-2,4-dioxo-1,2,3,4-tetrahydroquinoline;
7-chloro-2,4-dioxo-3-(3-methyl-2-furyl)-1,2,3,4-tetrahydroquinoline;
7-chloro-2,4-dioxo-3-(2-methyl-3-furyl)-1,2,3,4-tetrahydroquinoline;
7-chloro-2,4-dioxo-3-(4-isopropyl-2-furyl)-1,2,3,4-tetrahydroquinoline;
7-chloro-2,4-dioxo-3-(4-methyl-2-furyl)-1,2,3,4-tetrahydroquinoline;
7-chloro-2,4-dioxo-3-(5-phenyl-2-furyl)-1,2,3,4-tetrahydroquinoline;
7-chloro-2,4-dioxo-3-(5-methyl-2-thienyl)-1,2,3,4-tetrahydroquinoline;
3-(5-benzyl-2-thienyl)-7-chloro-2,4-dioxo-1,2,3,4-tetrahydroquinoline;
3-(3-benzo[b]thienyl)-7-chloro-2,4-dioxo-1,2,3,4-tetrahydroquinoline;
and salts and prodrugs thereof.

In addition, the following compounds are not specifically disclosed in the prior art, and are therefore novel compounds according to the present invention:
7-chloro-3-cyano-2,4-dioxo-1,2,3,4-tetrahydroquinoline;
2,4-dioxo-3-ethoxycarbonyl-6-nitro-1,2,3,4-tetrahydroquinoline;
7-chloro-2,4-dioxo-3-methoxycarbonyl-1,2,3,4-tetrahydroquinoline;
7-chloro-2,4-dioxo-3-n-propoxycarbonyl-1,2,3,4-tetrahydroquinoline;
6,7-dinitro-2,4-dioxo-3-ethoxycarbonyl-1,2,3,4-tetrahydroquinoline;
7-chloro-2,4-dioxo-3-ethoxycarbonyl-1,2,3,4-tetrahydroquinoline;
2,4-dioxo-3-ethoxycarbonyl-7-nitro-1,2,3,4-tetrahydroquinoline;
7-chloro-2,4-dioxo-3-n-pentyloxycarbonyl-1,2,3,4-tetrahydroquinoline;
7-chloro-2,4-dioxo-3-(2-propenyloxy)carbonyl-1,2,3,4-tetrahydroquinoline;
7-chloro-2,4-dioxo-3-ethoxycarbonyl-5-iodo-1,2,3,4-tetrahydroquinoline;
7-chloro-2,4-dioxo-5-ethyl-3-methoxycarbonyl-1,2,3,4-tetrahydroquinoline;
3-carboxy-7-chloro-2,4-dioxo-1,2,3,4-tetrahydroquinoline;
and salts and prodrugs thereof.

The present invention also provides pharmaceutical compositions comprising at least one of the novel compounds according to the invention in association with a pharmaceutically acceptable carrier.

The pharmaceutical compositions of this invention are preferably in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula IA above, including the novel compounds according to the invention, may be prepared by a process which comprises the reductive cyclisation of a compound of formula III:

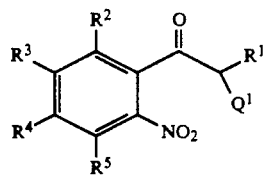

wherein $R^1$, $R^2$, $R^3$, $R^4$ and $R^5$ are as defined above; and $Q^1$ represents a reactive carboxylate moiety.

The reaction is conveniently carried out using hydrogen as reducing agent in the presence of a suitable hydrogenation catalyst such as palladium on charcoal, in an inert solvent such as ether, at room temperature at a pressure in the region of 50 p.s.i.

Suitable values for the reactive carboxylate moiety $Q^1$ include esters, for example $C_{1-4}$ alkyl esters; acid anhydrides, for example mixed anhydrides with $C_{1-4}$ alkanoic acids; acid halides, for example acid chlorides; orthoesters; and primary, secondary and tertiary amides.

Preferably, the group $Q^1$ represents methoxycarbonyl or ethoxycarbonyl.

The intermediates of formula III above may conveniently be prepared by reacting a compound of formula $Q^1$—$CH_2$—$R^1$ with a compound of formula IV:

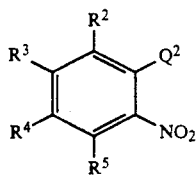

wherein $R^1$, $R^2$, $R^3$, $R^4$, $R^5$ and $Q^1$ are as defined above, and $Q^2$ represents a reactive carboxylate moiety; in the presence of a strong base.

For example, when $R^1$ represents a $C_{2-7}$ alkoxycarbonyl group, e.g. ethoxycarbonyl, the reagent of formula $Q^1$—$CH_2$—$R^1$ is suitably diethyl malonate, and the strong base employed will advantageously be magnesium ethoxide.

Suitable values for the reactive carboxylate moiety $Q^2$ correspond to those defined above for $Q^1$. Preferably, the group $Q^2$ is an acid halide group, in particular an acid chloride group. A compound of formula IV wherein $Q^2$ represents an acid chloride group may conveniently be prepared from the corresponding compound of formula IV wherein $Q^2$ represents a carboxy group —$CO_2H$ by treatment with thionyl chloride under standard conditions well known from the art.

In an alternative process, the compounds of formula IA above, including the novel compounds according to the invention, may be prepared by cyclisation of a compound of formula V:

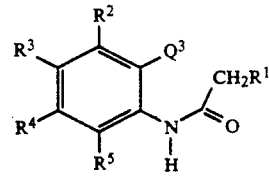

wherein $R^1$, $R^2$, $R^3$, $R^4$ and $R^5$ are as defined above; and $Q^3$ represents a reactive carboxylate moiety.

The cyclisation is conveniently effected by treatment of the compound of formula V with at least one equivalent of a strong base. The reaction conditions employed will vary depending upon the nature of the strong base utilised. For example, where potassium hexamethyldisilazide is utilised as the strong base, the reaction will suitably be effected at room temperature in tetrahydrofuran. Alternatively, where, for example, the strong base utilised is sodium methoxide or sodium ethoxide, the reaction will suitably be carried out at room temperature in an alcoholic solvent such as methanol or ethanol.

Suitable values for the reactive carboxylate moiety $Q^3$ correspond to those defined above for $Q^1$. Preferably, the group $Q^3$ is a $C_{1-4}$ alkyl ester such as methoxycarbonyl or ethoxycarbonyl.

The intermediates of formula V above may conveniently be prepared by reacting a compound of formula $Q^4$—$CH_2$—$R^1$ with a compound of formula VI:

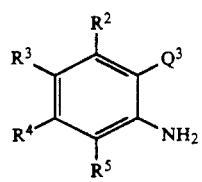

wherein $R^1$, $R^2$, $R^3$, $R^4$, $R^5$ and $Q^3$ are as defined above; and $Q^4$ represents a reactive carboxylate moiety.

The reaction is conveniently effected in dichloromethane at room temperature or in 1,2-dichloroethane at reflux temperature, advantageously in the presence of a mild organic base such as triethylamine and/or 4-dimethylaminopyridine.

Suitable values for the reactive carboxylate moiety $Q^4$ correspond to those defined above for $Q^1$. Preferably, the group $Q^4$ is an acid halide group, in particular an acid chloride group. An alternative preferred species of formula $Q^4$—$CH_2$—$R^1$ is the activated ester derivative formed upon reaction of the carboxy compound $HO_2C$—$CH_2$—$R^1$ with bis(2-oxo-3-oxazolidinyl)phosphinic chloride (BOP-Cl).

The aromatic intermediates of formulae IV and VI above, including the precursors of formula IV wherein $Q^2$ represents —$CO_2H$, where they are not commercially available, may be prepared by the methods described in the accompanying Examples, or by methods analogous thereto which will be readily apparent to those skilled in the art.

In a further process, the compounds of formula IA above, including the novel compounds according to the invention, may be prepared by reacting a compound of formula $Q^1$—$CH_2$—$R^1$ with a compound of formula VII:

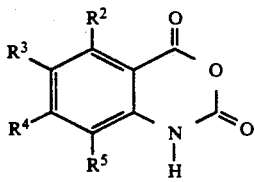

(VII)

wherein $R^1$, $R^2$, $R^3$, $R^4$, $R^5$ and $Q^1$ are as defined above; in the presence of a strong base such as sodium methoxide or sodium ethoxide.

The conditions for effecting this reaction are generally as described in *J. Med. Chem.*, 1976, 41, 825.

Where they are not commercially available, the intermediates of formula $Q^1$—$CH_2$—$R^1$ and $Q^4$—$CH_2$—$R^1$ may be prepared by methods analogous to those described in the accompanying Examples, or by standard procedures well known from the art.

It will be appreciated that any compound of formula IA or IB initially obtained from any of the above processes may, where appropriate, subsequently be elaborated into a further desired compound of formula IA or IB respectively.

For example, a compound of formula IA or IB initially obtained wherein $R^1$ represents a group of formula —$CO_2R^6$ may subsequently be converted into the desired compound of formula IA or IB wherein $R^1$ represents a different group —$CO_2R^6$ by conventional transesterification procedures known from the art. In particular, it has been found in many cases that this transesterification can be brought about simply by heating the ester of formula IA or IB initially obtained, at a temperature in excess of 130° C., in an alcohol of formula $R^6OH$ in which $R^6$ represents the residue of the ester group —$CO_2R^6$ in the desired final product of formula IA or IB, the alcohol $R^6OH$ itself simultaneously serving as the solvent.

Alternatively, a compound of formula IA or IB wherein $R^1$ represents a five-membered heteroaromatic ring containing the ring atoms W to Z as defined above may suitably be prepared from a corresponding compound of formula IA or IB wherein $R^1$ represents —$CO_2R^6$ by standard methods well known from the art.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-tolyoyl-d-tartaric acid and/or (+)-di-p-toluoyl-l-tartaric acid followed by fractional crystallization and regeneration of the free base. The compounds may also be resolved by formation of diastereomeric esters and amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

The compounds useful in this invention potently and selectively block responses to NMDA and/or AMPA in a brain slice from rat cortex, and inhibit glycine binding to the strychnine-insensitive site present on the NMDA receptor and/or AMPA binding to rat forebrain membranes.

CORTICAL SLICE STUDIES

The effects of compounds of the invention on responses to NMDA and AMPA were assessed using the rat cortical slice as described by Wong et al., *Proc. Natl. Acad. Sci. USA*, 1986, 83, 7104. The apparent equilibrium constant ($K_b$) was calculated from the righthand shift in the NMDA or AMPA concentration-response curves produced by the compound under test. Of those compounds of the accompanying Examples which were tested, all were found to possess a $K_b$ value in response to NMDA of below 150 μM. The compounds of Examples 49 and 50 were tested and were found to possess a $K_b$ value in response to AMPA of below 150 μM in each case.

BINDING STUDIES

The ability of test compounds to displace either $^3$H-glycine binding or $^3$H-L-689,560 (trans-2-carboxy-5,7-dichloro-4-phenylaminocarbonylamino-1,2,3,4-tetrahydroquinoline) binding to the strychnine-insensitive site present on the NMDA receptor of rat forebrain membranes was determined. $^3$H-Glycine binding was measure by the method of Donald et al., *Proceedings of The British Pharmacological Society*, University of Nottingham, September 1988, Abstract P122. For $^3$H-L-689,560 binding, 100 μm of membrane protein was incubated at 4° C. for 45 or 120 min with 50 mM Tris-acetate buffer (pH 7.0) and 1 nM $^3$H-L-689,560 in a final volume of 0.5 ml. Non-specific binding was determined with 1 mM glycine and bound radioactivity was separated by filtration through Whatman GF/B filters. The concentration of the compounds of the accompanying Examples required to displace 50% of the specific binding of either tritiated ligand ($IC_{50}$) could thereby be derived. Of those compounds which were tested, all were found to possess an $IC_{50}$ value of below 50 μM.

The ability of test compounds to displace $^3$H-AMPA binding to rat forebrain membranes was determined by the method of Honore et al., *Neurosci. Lett.*, 1985, 54, 27. The compound of accompanying Example 50 was tested and was found to possess an $IC_{50}$ value of below 50 μM.

WHOLE-CELL PATCH-CLAMP STUDIES

The ability of test compounds to block the potentiation of NMDA responses by glycine in cultured cortical neurones was measured using patch-clamp techniques as described by Foster and Kemp, *J. Neurosci.*, 1989, 9, 2191. The compound of accompanying Example 26 was tested and was active at concentrations below 20 μM.

EXAMPLE 1

Step 1: 2-Ethoxycarbonyl-5-chloro-phenylisocyanate

A solution of phosgene in toluene (36.3 ml×20%) was added dropwise over 30 min to a stirred solution of ethyl-4-chloroanthranilate (10.0 g) and triethylamine (15 ml) in dry tetrahydrofuran at −5° C. The temperature was maintained at −5° C. for 1 h and then allowed to warm to room temperature. After 1 h ether (200 ml) was added and the solution filtered. Removal of solvent under reduced pressure afforded the product as a white solid (11.2 g). δ(CDCl$_3$) 1.39 (3H, t, J=7.5 Hz, CH$_2$CH$_3$), 4.34 (2H, q, J=7.5 Hz, CH$_2$CH$_3$), 7.22 (1H, d, J=CH$_2$CH$_3$, 1.0 Hz, H-6), 7.28 (1H, dd, J=6.5 and 1.0 Hz, H-4), 8.31 (1H, d, J=6.5 Hz, H-3); m/z (EI+) 225.

Step 2:
3-(3-Thienoyl)-7-chloro-2,4-dioxo-1,2,3,4-tetrahydroquinoline

3-Acetylthiophene (1.1 g) in dry tetrahydrofuran (10 ml) was added dropwise to a solution of lithium hexamethyldisilazide (9.0 ml×10 mol) in dry tetrahydrofuran (20 ml) at −78° C. The resulting solution was allowed to warm to 0° C. over 30 min and then re-cooled to −78° C. A solution of 2-ethoxycarbonyl-5-chlorophenylisocyanate (1.0 g) in dry tetrahydrofuran (10 ml) was added dropwise over 15 min. The temperature was maintained at −78° C. for 30 min and then allowed to warm to room temperature. After 2 h the reaction mixture was poured into 1N HCL (50 ml), extracted with ether (4×50 ml), washed with water (50 ml) and brine (50 ml), dried over MgSO$_4$, filtered and the solvent removed under reduced pressure to afford a brown solid. Recrystallisation from methanol gave the product as pale yellow needles (740 mg) mp 260°–263° C.; δ(CDCl$_3$) 1.4 (3H, t, J=7.5 Hz, CH$_2$CH$_3$), 4.02 (2H, s, CH$_2$CO), 4.4 (2H, q, J=7.5 Hz, CH$_2$CH$_3$), 7.05 (1H, dd, J=8.5 and 1.0 Hz, H-6), 7.1 (1H, m, 5-CH—CH), 7.4 (1H, m, 5-CH—CH), 7.45 (1H, d, J=8.5 Hz, H-5), 8.01 (1H, m, 5-CH—C), 8.8 (1H, d, J=1.0 Hz, H-8). Sodium methoxide (61.4 g) was added to a suspension of this compound (200 mg) in dry methanol (20 ml). The resulting mixture was warmed to reflux for 18 h. The reaction mixture was cooled to room temperature and poured into 1N HCl (50 ml). The resulting precipitate was filtered off and recrystallised from dimethylformamide to afford the product as pale yellow needles. mp 313°–320° C. (dec); (Found: C, 54.67; H, 2.63; N, 4.66 C$_{14}$H$_8$NO$_3$SCl+0.1H$_2$O requires C, 54.67; H, 2.68; N, 4.55%); δ(d$_6$-DMSO) 7.23 (1H, dd, J=9.5, 1.0 Hz, H-6), 7.33 (1H, d, J=1.0 Hz, H-8), 7.45 (1H, dd, J=5.5 and 1.0 Hz, 5-CH—CH), 7.56 (1H, dd, J=5.5 and 2.0 Hz, 5-CH—CH), 7.95 (1H, d, J=9.5 Hz, H-5), 8.26 (1H, dd, J=2.0 and 1.0 Hz, 5-CH—C); m/z (EI+) 305. The following compounds were made by the same method (Method A), typified by Example 1, Step 2 above.

EXAMPLE 2

7-Chloro-3-(2-furanoyl)-2,4-dioxo-1,2,3,4-tetrahydroquinoline

Yellow needles mp 310° C.; (Found: C, 57.90; H, 2.70; N, 4.65; C$_{14}$H$_8$ClNO$_4$ requires C, 58.05; H, 2.78; N, 4.84%); δ(d$_6$ DMSO) 6.69 (1H, dd, J=3.6 and 1.5 Hz—OCHCH—), 7.24 (1H, dd, J=8.5 and 2.0 Hz, H-6), 7.33 (2H, —OCHCHCH—, H-8), 7.94 (1H, d, J=8.5 Hz, H-5), 7.99 (1H, d, J=1.5 Hz, —OCH), 11.57 (1H, br s, NH).

EXAMPLE 3

7-Chloro-2,4-dioxo-3-(2-thienoyl)-1,2,3,4-tetrahydroquinoline

Yellow needles mp 314°–315° C.; (Found: C, 54.68; H, 2.52; N, 4.54; C$_{14}$H$_8$CLNO$_3$S. 0.05 H$_2$O requires C, 54.84; H, 2.66; N, 4.57%); δ(d$_6$ DMSO) 7.18 (1H, dd, J=5.0 Hz and 4.0 Hz, —5CHCH—), 7.31 (1H, dd, J=8.5 Hz and 2.0 Hz, H-6), 7.34 (1H, d, J=2.0 Hz, H-8), 7.71 (1H, dd, J=4.0 Hz and 1.0 Hz, —SCHCH—), 7.52 (1H, d, J=8.5 Hz, H-5), 8.02 (1H, dd, J=5.0 Hz and 1.0 Hz, —SCH), 11.64 (1H, br s, NH).

EXAMPLE 4

7-Chloro-3-[3-(2,5-dimethylfuranoyl)]-2,4-dioxo-1,2,3,4-tetrahydroquinoline

Yellow needles mp 254°–256° C.; (Found: C, 60.22; H, 3.80; N, 4.43. C$_{16}$H$_{12}$ClNO$_4$ requires C, 60.48; H, 3.81; N, 4.41%); δ(DMSO d$_6$) 2.21 (3H, s, —CH$_3$), 2.40 (3H, s, CH$_3$), 6.20 (1H, s, OCCH), 7.24 (1H, dd, J=8.5 Hz and 2.0 Hz, H-6), 7.32 (1H, d, J=2.0 Hz, H-8), 7.94 (1H, d, J=8.5 Hz, H-5), 11.58 (1, br s, NH). m/z (EI+) 317 (M+).

EXAMPLE 5

7-Chloro-3-[2-(5-methylfuranoyl)]-2,4-dioxo-1,2,3,4-tetrahydroquinoline

Yellow needles mp 272° C. (dec); (Found: C, 59.33; H, 3.09; H, 4.57. C$_{15}$H$_{14}$ClNO$_4$ requires C, 59.32; H, 3.32; N, 4.61%) δ(DMSO d$_6$) 2.38 (3H, s, —CH$_3$), 6.35 (1H, d, J=3.5 Hz, MeCCH), 7.24 (1H, dd, J=8.5 Hz and 2.0 Hz, H-6), 7.26 (1H, d, J=3.5 Hz, MeCCHCH), 7.32 (1H, d, J=2.0 Hz, H-8), 7.92 (1H, d, J=8.5 Hz, H-5), 11.58 (1H, br s, —NH); m/z (EI+) 303 (M+).

EXAMPLE 6

7-Chloro-3-[2-(5-nitrobenzofuranoyl)]-2,4-dioxo-1,2,3,4-tetrahydroquinoline

Yellow needles mp 320° C. (dec); (Found: C, 55.96; H, 2.14; N, 7.36. C$_{18}$H$_9$Cl N$_2$O$_6$ requires C, 56.20; H, 2.36; N, 7.28%), 7.27 (1H, dd, J=8.5 Hz and 2.0 Hz, H-6), 7.35 (1H, d, J=2.0 Hz, H-8), 7.92 (1H, s, benzofuran H-3), 7.97 (1H, d, J=8.5 Hz, H-5), 7.99 (1H, d, J=9.0 Hz, benzofuran H-7), 8.38 (1H, dd, J=9.0 Hz and 2.5 Hz, benzofuran H-6), 8.76 (1H, d, J=2.5 Hz, benzofuran H-4), 11.66 (1H, br, s, NH); m/z (CI+, NH$_3$), 385 (M+ +H).

EXAMPLE 7

3-(2-Benzofuranoyl)-7-chloro-2,4-dioxo-1,2,3,4-tetrahydroquinoline

Yellow needles mp 295° C.; (Found: C, 65.58; H, 2.84; N, 4.08. C$_{18}$H$_{10}$NO$_4$ requires C, 65.64; H, 2.97; N, 4.12%); δ(DMSO d$_6$) 7.26 (1H, dd, J=8.5 Hz and 2.0 Hz, H-6), 7.35 (2H, m, J=7.5 Hz, J=2.0 Hz, Ar—H, H-8), 7.56 (1H, td, J=8.5 Hz and 1.0 Hz, Ar—H), 7.72 (1H, d, J=8.5 Hz, Ar—H), 7.75 (1H, s, OCCH), 7.79 (1H, d, J=7.5 Hz, Ar—H), 7.96 (1H, d, J=8.5 Hz, H-5), 11.65 (1H, br s, NH); m/z (EI+) 339 (M+).

EXAMPLE 8

3-(3-Benzo[b]thienoyl)-7-chloro-2,4-dioxo-1,2,3,4-tetrahydroquinoline

A solution of 3-acetylbenzo[b]thiophene (1.54 g) in dry tetrahydrofuran (10 ml) was added dropwise to a solution of potassium hexamethyldisilazide (17.5 ml×0.5M) in dry tetrahydrofuran at −78° C. The resulting solution was allowed to warm to 0° C. over 30 min and then re-cooled to −78° C. A solution of 2-ethoxycarbonyl-5-chlorophenyl isocyanate (1.0 g) in dry tetrahydrofuran (10 ml) was added dropwise over 15 min. The temperature was maintained at −78° C. for 30 min, and then warmed to room temperature. After 2 h the reaction mixture was poured into IN HCl (100 ml) and the precipitate filtered off. Recrystallisation from dimethylformamide afforded the product as yellow needles. mp 306°-307° C.; (Found: C, 59.85; H, 2.69; N, 3.99. $C_{18}H_{10}NO_3SCl\ 0.3H_2O$ requires C, 59.85; H, 2.95; N, 3.88%); $\delta(d_6\text{-DMSO})$ 7.20 (1H, dd, J=6.0 and 1.0 Hz, H-6), 7.36 (1H, d, J=1.0 Hz, H-8), 7.48-7.52 (2H, m, H-5' and H-6'), 7.96 (1H, d, J=6.0 Hz, H-5), 8.01 (1H, d, J=5.0 Hz, H-4'), 8.45 (1H, s, H-2'), 8.47 (1H, d, J=5.0 Hz, H-7'); m/z (EI+) 355.

The following compounds were made by the same general method(Method B), typified by Example 8 above.

EXAMPLE 9

3-(2-Phenylacetyl)-7-chloro-2,4-dioxo-1,2,3,4-tetrahydroquinoline

White needles m.p. 174°-176° C.; (Found: C, 62.28; H, 4.01; N, 4.87. $C_{17}H_{17}NO_3Cl+0.75H_2O$ requires: C, 62.40; H, 4.15; N, 4.30%); $\delta(CDCl_3)$, 3.80 (2H, s, Ar—CH$_2$), 7.05 (1H, dd, J=6.0 and 1.0 Hz, H-6), 7.0 (5H, m, 5×Ar—H), 7.99 (1H, d, J=6.0 Hz, H-5), 8.82 (1H, d, J=1.0 Hz, H-8), 10.6 (1H, br s, NH).

EXAMPLE 10

3-(2-[5-Methylthienoyl])-7-chloro-2,4-dioxo-1,2,3,4-tetrahydroquinoline

White needles m.p. 302°-303° C.; (Found: C, 55.74; H, 2.80; N, 4.49. $C_{15}H_{10}NO_3SCl+0.1H_2O$ requires: C, 56.03; H, 3.19; N, 4.36%); $\delta(d_6\text{-DMSO})$ 2.51 (3H, s, CH$_3$), 6.90 (1H, d, J=1.5 Hz, CH$_3$C—CH), 7.24 (1H, dd, J=5.5 and 1.0 Hz, H-6), 7.31 (1H, d, J=1.0 Hz, H-8), 7.54 (1H, d, J=1.5 Hz, SC—CH), 7.93 (1H, d, J=5.5 Hz, H-5); m/z (EI+) 318.

EXAMPLE 11

3-(2-[3-Methylthienoyl])-7-chloro-2,4-dioxo-1,2,3,4-tetrahydroquinoline

White needles m.p. 260°-261° C.; (Found: C, 55.59; H, 2.97; N, 4.57. $C_{15}H_{10}NO_3SCl+0.2H_2O$ requires: C, 55.71; H, 3.24; N, 4.33%); $\delta(d_6\text{-DMSO})$ 2.4 (3H, s, CH$_3$), 7.05 (1H, d, J=4.5 Hz, CH$_3$C—CH), 7.25 (1H, dd, J=6.5 and 1.0 Hz, H-6), 7.3 (1H, d, J=1.0 Hz, H-8), 7.85 (1H, d, J=4.5 Hz, 5'-CH), 7.95 (1H, d, J=6.5 Hz, H-5), 11.85 (1H, s, NH); m/z (EI+) 318.

EXAMPLE 12

3-(3-[2,5-Dimethylthienoyl])-7-chloro-2,4-dioxo-1,2,3,4-tetrahydroquinoline

White needles m.p. 224°-225° C.; (Found: C, 57.60; H, 3.25; N, 4.05. $C_{16}H_{12}NO_3SCl$ requires: C, 57.57; HG, 3.62; N, 4.20%); $\delta(d_6\text{-DMSO})$ 2.25 (3H, s, CH$_3$), 2.5 (3H, s, CH$_3$), 6.8 (1H, s, 5-CCH), 7.2 (1H, dd, J=7.0 and 1.0 Hz, H-6), 7.25 (1H, d, J=1.0 Hz, H-8), 7.95 (1H, d, J=7.0 Hz, H-5), 11.6 (1H, s, NH); m/z (EI+) 333.

EXAMPLE 13

(E)-3-(3-[3-Thienyl]-2-propen-1-oyl)-7-chloro-2,4-dioxo-1,2,3,4-tetrahydroquinoline White needles m.p. 320°-322° C.; (Found: C, 57.72; H, 2.84; N, 4.21. $C_{16}H_{10}NO_3SCl$ requires: C, 57.92; H, 3.04; N, 4.22%); $\delta(d_6\text{-DMSO})$, 7.24 (1H, dd, J=7.0 and 1.0 Hz, H-6), 7.31 (1H, s, CH—CHCH), 7.46 (1H, d, J=1.0 Hz, H-8), 7.66 (1H, d, J=4.5 Hz, 5-CH—CH), 7.93 (1H, d, J=9.5 Hz, C—CHCH—CO), 7.96 (1H, d, J=7.0 Hz, H-5), 8.01 (1H, d, J=4.5 Hz, 5-CH—CH), 8.34 (1H, d, J=9.5 Hz, C—CH—CH—CO); m/z (EI+) 331.

EXAMPLE 14

3-(2-[5-Bromothienoyl])-7-chloro-2,4-dioxo-1,2,3,4-tetrahydroquinoline

White needles m.p. 309°-310° C.; (Found: C, 43.75; H, 1.64; N, 3.72. $C_{14}H_7NO_3Cl\ Br$ requires: C, 43.71; H, 1.83; N, 3.64%); $\delta(d_6\text{-DMSO})$ 7.25 (1H, dd, J=6.0 and 1.0 Hz, H-6), 7.32 (1H, d, J=3.0 Hz, Br—CH), 7.34 (1H, d, J=1.0 Hz, H-8), 7.59 (1H, d, J=3.0 Hz, SC—CH), 7.94 (1H, d, J=6.0 Hz, H-5); m/z (EI+) 384.

EXAMPLE 15

7-Chloro-3-[2-(1-methylpyrroloyl)]-2,4-dioxo-1,2,3,4-tetrahydroquinoline

Yellow needles m.p.>300° C.; (Found: C, 59.13; H, 3.72; N, 9.03; $C_{15}H_{11}ClN_2O_3+0.1\ H_2O$ requires C, 59.16; H, 3.71; N, 9.20%); $\delta(d_6\ DMSO)$ 3.94 (3H, s, —CH$_3$), 6.05 (1H, dd, J=4.0 Hz and 2.5 Hz, —NHCHCH), 6.63 (1H, dd, J=4.0 Hz and 1.5 Hz, —NCHCHCH), 7.17 (1H, dd, J=2.5 Hz and 1.5 Hz, —NCH), 7.21 (1H, dd, J=8.5 Hz and 2.0 Hz, H-6), 7.30 (1H, d, J=2.0 Hz, H-8), 7.90 (1H, d, J=8.5 Hz, H-5), 11.48 (1H, br s, NH); m/z (EI+) 302 (M+).

EXAMPLE 16

7-Chloro-3-[3-(1-methylpyrroloyl)]-2,4-dioxo-1,2,3,4-tetrahydroquinoline

Yellow needles m.p. 272° C. dec; (Found: C, 59.33; H, 3.38; N, 9.01; $C_{15}H_{11}ClN_2O_3$ requires C, 59.52; H, 3.66; N, 9.25%); $\delta(d_6\ DMSO)$ 3.65 (3H, s, —CH$_3$), 6.58 (1H, m, NCHCH), 6.78 (1H, m, NCHCH), 7.23 (1H, dd, J=8.5 Hz and 2.0 Hz, H-6), 7.31 (1H, d, J=2.0 Hz, C-8), 7.70 (1H, br s, NCH), 7.94 (1H, br s, NCH), 7.94 (1H, d, J=8.5 Hz, H-5), 11.42 (1H, br s, NH); m/z (EI+) 302 (M+).

EXAMPLE 17

7-Chloro-[3-(1-methylindoloyl)]-2,4-dioxo-1,2,3,4-tetrahydroquinoline

Yellow needles, m.p. 282° C. (dec); (Found: C, 64.55; H, 3.35; H, 7.85 $C_{19}H_{13}ClN_2O_4$ requires C, 64.69; H, 3.71; N, 7.94%); $\delta(DMSO\ d_6)$, 3.84 (3H, s, —CH$_3$), 7.22-7.32 (3H, m, 3×Ar—H), 7.35 (1H, d, J=2.0 Hz, H-8), 7.55 (1H, dd, J=6.0 Hz and 2.0 Hz, Ar—H), 7.96 (1H, d, J=8.5 Hz, H-5), 8.23 (2H, m, Ar—H, NCH), 11.52 (1H, br s, NH); m/z (EI+) 352 (M+).

EXAMPLE 18

3-(Cyclopropanecarbonyl)-7-chloro-2,4-dioxo-1,2,3,4-tetrahydroquinoline

White needles m.p. 227°-230° C.; (Found: C, 58.98; H, 3.81; N, 5.19. $C_{13}H_{10}NO_3Cl$ requires C, 59.22; H, 3.82; N, 5.31%); $\delta(d_6\text{-DMSO})$, 1.2-1.28 (4H, m, CH$_2$CH$_2$), 3.96-4.01 (1H, m, COCHCH$_2$), 7.26 (1H, dd, J=9.0 and 1.5 Hz, H-6), 7.31 (1H, d, J=1.5 Hz, H-8), 7.97 (1H, d, J=9.0 Hz, H-5), 11.63 (1H, br s, NH); m/z (EI+) 264.

EXAMPLE 19

3-(5'-[2'-Methylfuranyl])-7-chloro-2,4-dioxo-1,2,3,4-tetrahydroquinoline

Triethylamine (1.04 ml) was added to a stirred solution of bis(2-oxo-3-oxazolidinyl)phosphinic chloride (1.03 g), methyl-4-chloroanthranilate (0.68 g) and 5-methylfuranyl-2-acetic acid (0.52 g) in 1,2-dichloroethane (50 ml). The solution was warmed to reflux overnight. The reaction mixture was cooled to room temperature and washed with water. The organic layer was separated, dried over $MgSO_4$, filtered and the solvent removed under reduced pressure. Chromatography on silica gel using 10% ethyl acetate in n-hexane as eluant afforded the product as a white solid (0.66 g) $\delta(CDCl_3)$ 2.28 (3H, s, Ar—$CH_3$), 3.86 (2H, s, $CH_2CONAr$), 3.95 (3H, s, $CO_2CH_2$), 5.95 (1H, d, J=2.0 Hz, $CH_3C$—CHCH), 6.05 (1H, d, J=2.0 Hz, $CH_3C$—CHCH), 7.01 (1H, dd, J=7.0 and 1.0 Hz, ArH), 7.95 (1H, d, J=7.0 Hz, ArH), 8.80 (1H, d, J=1.0 Hz, ArH). Potassium hexamethyldisilazane (11.1 ml of a 0.5 mol solution in toluene) was added to a stirred solution of this compound (0.66 g) in dry tetrahydrofuran (20 ml) at room temperature. The resulting solution was stirred at room temperature for 1.5 hours. At the end of this time methanol (20 ml) was added and the solution evaporated to dryness under reduced pressure. The residual solid was redissolved in methanol (20 ml) and 1N HCl added. The resulting precipitate was filtered off and recrystallized from dimethylformamide to afford the title compound as white needles (0.26 g) m.p. 281°-282° C. (Found: C, 60.44; H, 3.55; N, 4.84 $C_{14}H_{10}MO_3Cl+0.1 H_2O$ requires C, 60.60; H, 3.70; N, 5.04%), $\delta(d_6$-DMSO), 2.55 (3H, s, $ArCH_3$), 6.19 (1H, d, J=1.0 Hz, $CH_3C$—CHCH), 6.86 (1H, d, J=1.0 Hz, $CH_3$—C—CHCH), 7.21 (1H, dd, J=6.0 and 1.0 Hz, H-6), 7.24 (1H, d, J=1.0 Hz, H-8), 7.91 (1H, d, J=6.0 Hz, H-5).

The following compounds were made by the same method (Method C), typified by Example 19 above.

EXAMPLE 20

3-(2'[5'-Ethylfuryl])-7-chloro 2,4 dioxo-1,2,3,4-Tetrahydroquinoline

White needles m.p. 263°-265° C. (Found: C, 62.48; H, 3.81; N, 4.58. $C_{15}H_{12}NO_3Cl$ requires C, 62.19; H, 4.18; N, 4.83%); $\delta(d_6$-DMSO) 130 (3H, t, J=7.0 Hz, $CH_2CH_3$), 2.77 (2H, q, J=7.0 Hz, $CH_2CH_3$), 6.18 (1H, d, J=1.5 Hz, $CH_3$—CCH), 7.14 (1H, dd, J=7.0 and 1.0 Hz, H-6), 7.31 (1H, d, J=1.5 Hz, CHCHC), 7.34 (1H, d, J=1.0 Hz, H-8), 7.91 (1H, d, J=7.0 Hz, H-5); m/z (EI+) 289.

EXAMPLE 21

3-(2'-[1'-Methylpyrrolyl])-7-chloro-2,4-dioxo-1,2,3,4-tetrahydroquinoline

White needles m.p. 340° C.; (Found: C, 59.60; H, 4.11; N, 10.02 $C_{14}H_{11}N_3O_2Cl$ requires C, 59.65; H, 4.22; N, 9.94%); $\delta(d_6$-DMSO) 3.41 (3H, s, $NCH_3$), 5.97-6.02 (1H, m, H-5'), 6.05-6.10 (1H, m, H-4'), 6.84-6.91 (1H, m, H-3'), 7.20 (1H, dd, J=7.2 and 2.0 Hz, H-6), 7.32 (1H, d, J=2.0 Hz, H-8), 7.88 (1H, d, J=7.2 Hz, H-5), 10.18 (1H, br s, NH).

EXAMPLE 22

3-(2'-Furanyl)-7-chloro-2,4-dioxo-1,2,3,4-tetrahydroquinoline

White needles m.p. 246°-250° C.; $\delta(d_6$-DMSO) 6.60 (1H, m, H-4'), 6.98 (1H, dd, J=4.0 and 1.0 Hz, H-3'), 7.24 (1H, dd, J=9.0 and 1.5 Hz, H-6), 7.34 (1H, d, J=1.5 Hz, H-8), 7.74 (1H, d, J=1.0 Hz, H-5'), 7.96 (1H, d, J=9.0 Hz, H-5), 11.66 (1H, s, NH).

EXAMPLE 23

3-(2'-[4'-Benzoyl-1'-methylpyrrolyl])-7-chloro-2,4-dioxo 1,2,3,4 Tetrahydroquinoline White needles m.p. 282°-284° C. (Found: C, 65.49; H, 3.80; N, 7.09. $C_{21}H_{15}N_2O_3Cl$ requires C, 65.64; H, 4.09; N, 7.29%); $\delta(d_6$-DMSO) 3.50 (3H, s. $NCH_3$). 6.48 (1H, d, J=1.0 Hz, COCCHC), 7.08 (1H, dd, J=6.0 and 1.0 Hz, H-6), 7.17 (1H, d, J=1.0 Hz, $CH_3N$—CH), 7.44-7.62 (3H, m, 3×Ar—H), 7.75-7.81 (2H, m, 2×Ar—H), 7.96 (1H, d, J=6.0 Hz, H-6); m/z (EI+) 378.

EXAMPLE 24

3-(2'-[5'-Benzoyl-1'-methylpyrroloyl])-7-chlor-2,4-dioxo 1,2,3,4 Tetrahydroquinoline White needles m.p. 295°-296° C. (Found: C, 65.30; H, 3.89; N, 7.13. $C_{21}H_{15}N_2O_3Cl+0.4 H_2O$ requires C, 65.34; H, 4.12; N, 7.25%); $\delta(d_6$-DMSO) 3.78 (3H, s, $NCH_3$), 6.08 (1H, d, J=1.0 Hz, C—CHCH), 6.70 (1H, d, J=1.0 Hz, C—CHCH), 7.24 (1H, dd, J=7.5 and 1.0 Hz, H-6), 7.4-7.48 (3H, m, 3×Ar—H), 7.6-7.7 (2H, m, 2×ArH), 7.95 (1H, d, J=7.5 Hz, H-5); m/z (EI+) 378.

EXAMPLE 25

Ethyl 7-Chloro-2,4-dioxo-3-(1,2,3,4-tetrahydroquinoline)carboxylate

Ethyl malonyl chloride (26 ml) in dry dichloromethane (100 ml) was added dropwise over 1 h to a stirred solution of ethyl 4-chloroanthranilate (20.4 g), triethylamine (43 ml) and 4-dimethylaminopyridine (0.5 g) in dry dichloromethane (300 ml) at 0° C. After 1 h triethylamine (43 ml) was added, then ethyl malonyl chloride (26 ml) in dry dichloromethane (100 ml) added over 1 h. The suspension was evaporated in vacuo, diluted with ethyl acetate, washed twice with 1M citric acid, then saturated sodium bicarbonate solution, water and brine, dried ($MgSO_4$) and evaporated in vacuo to give an oil (53 g). 47 g of this oil was dissolved in ethanol (500 ml) then sodium methoxide (16.2 g) was added. After 30 min the mixture was diluted with water, washed with ethyl acetate, and the aqueous layer acidified with concentrated hydrochloric acid. The resulting precipitate was collected and dried to give 19 g of white solid. 17 g of this solid was recrystallised from dimethyl formamide (300 ml), keeping the temperature below 100° C., then washed with water, ethanol and ether, and dried to give the ester (8.81 g) as white needles, m.p. >340° C.; (Found: C, 53.68; H, 3.78; N, 5.28. $C_{12}H_{10}NO_4Cl$ requires C, 53.85; H, 3.77; N, 5.23%), $\delta(d_6$-DMSO) 13.3 (1H, br s), 11.58 (1H, s), 7.92 (1H, d, J=8.6 Hz, H-5), 7.30 (1H, d, J=1.9 Hz, H-8), 7.24 (1H, dd, J=1.9 and 8.6 Hz, H-6), 4.33 (2H, q, J=7.1 Hz, $CH_2$), 1.30 (3H, t, J 7.1 Hz, $CH_3$); m/z (EI+) 267 (M+).

EXAMPLE 26

Methyl 7-Chloro-2,4-dioxo-3-(1,2,3,4-tetrahydroquinoline)carboxylate

Ethyl 7-chloro-2,4-dioxo-3-(1,2,3,4-tetrahydroquinoline)carboxylate (0.42 g) and dry methanol (25 ml) were heated in a sealed apparatus with an internal temperature of 130° C. for 20 min. The mixture was cooled, the solid collected and recrystallised from dimethylformamide, keeping the temperature below 110° C., to give the ester (107 mg) as white needles, sublimes 240° C.; (Found: C, 52.04; H, 3.27; N, 5.63. $C_{11}H_8NO_4Cl$ requires C, 52.09; H, 3.18; N, 5.52%); $\delta$($d_6$-DMSO) 11.60 (1H, s), 7.93 (1H, d, J=8.6 Hz, H-5), 7.29 (1H, d, J=2.0 Hz, H-8), 7.24 (1H, dd, J=2.0 and 8.6 Hz, H-6), 3.85 (3H, s, $CH_3$); m/z (EI+) 253 (M+).

EXAMPLE 27

Propyl 7-Chloro-2,4-dioxo-3-(1,2,3,4-tetrahydroquinoline)carboxylate

Ethyl 7-chloro-2,4-dioxo-3-(1,2,3,4-tetrahydroquinoline)carboxylate (0.42 g) and 1-propanol (4 ml) were heated in a sealed apparatus with an internal temperature of 160° C. for 20 min. The mixture was cooled and the ester collected as fine white needles, m.p.>320° C. (Found: C, 55.39; H, 4.32; N, 4.96. $C_{13}H_{12}NO_4Cl$ requires C, 55.43; H, 4.29; N, 4.97%); $\delta$($d_6$-DMSO) 11.48 (1H, s), 7.92 (1H, d, J=8.6 Hz, H-5), 7.29 (1H, d, J=0.6 Hz, H-8), 7.23 (1H, dd, J=0.6 and 8.6 Hz, H-6), 4.23 (2H), t, J=7 Hz, $OCH_2$), 1.69 (2H, sextet, J=7 Hz, $OCH_2CH_2$), 0.97 (3H, t, J=7 Hz, $CH_3$); m/z (CI+, $NH_3$) 282 (M++H).

EXAMPLE 28

7-Chloro-3-cyano-2,4-dioxo-1,2,3,4-tetrahydroquinoline n-Butyl chloroformate (1.5 ml) was added to cyanoacetic acid (1 g) and triethylamine (1.65 ml) in dry dichloromethane (20 ml) at −23° C. After 15 min ethyl 4-chloroathranilate (901 mg), triethylamine (1.65 ml) and 4-dimethylaminopyridine (100 mg) in dry dichloromethane (7 ml) were added. After stirring at −23° C. for 15 min the mixture was brought to 0° C. for 1 h, then diluted with ethyl acetate, washed with 1M citric acid, saturated sodium bicarbonate solution, water, and brine, dried (MgSO$_4$), evaporated in vacuo, and purified by flash chromatography to give ethyl 2-cyanoacetamido-4-chlorobenzoate as a white solid (214 mg). 190 mg of this solid was suspended in methanol (10 ml) and sodium methoxide (50 mg) added. After stirring at room temperature for 30 min the mixture was acidified with 1M hydrochloric acid, extracted with ethyl acetate (×3), the combined organic layers washed with water and brine, dried (MgSO$_4$) and evaporated in vacuo to give the tetrahydroquinoline (81 mg) as long needles m.p. 314°–316° C. (from dimethylformamide/ethyl acetate/hexanes); (Found: C, 54.27; H, 2.41; N, 12.70. $C_{10}H_5N_2O_2Cl$ requires C, 54.44; H, 2.28; N, 12.70%); $\delta$($d_6$-DMSO) 11.63 (1H, s), 7.97 (1H, d, J=8.6 Hz, H-5), 7.29 (1H, d, J=1.8 Hz, H-8), 7.24 (1H, dd, J=1.8 and 8.6 Hz, H-6); m/z (CI+, $NH_3$) 221 (M++H).

The following examples were made by the same method (Method D): Typically, ethyl 7-chloro-2,4-dioxo-3-(1,2,3,4-tetrahydroquinoline)carboxylate (0.4 g), and the relevant alcohol (1 g) were heated together at 140° C. for 20 min, cooled, ethyl acetate added, and the solid collected, dried and recrystallised.

EXAMPLE 29

3-(4-Hydroxyphenyl)-1-propyl 7-Chloro-2,4-dioxo-3-(1,2,3,4-tetrahydroquinoline)carboxylate White solid, m.p. 210°–211° C. (from dimethylformamide/acetone/water); (Found: C, 60.92; H, 4.42; N, 3.78. $C_{19}H_{16}NO_5Cl$ requires C, 61.05; H, 4.32; N, 3.75); $\delta$($d_6$-DMSO) 13.3 (1H, br s), 11.55 (1H, s), 9.11 (1H, s), 7.93 (1H, d, J=8.7 Hz, H-5), 7.31 (1H, d, J=1.7 Hz, H-8), 7.24 (1H, dd, J=1.7 and 8.7 Hz, H-6), 7.02 (2H, d, J=8.4 Hz, CHCHCOH), 6.67 (2H, d, J=8.4 Hz, CHCOH), 4.24 (2H, t, J=6.5 Hz, $CH_2OCO$), 2.63 (2H, t, J=6.5 Hz, $CH_2Ar$), 1.92 (2H, quintet, J=6.5 Hz, $CH_2CH_2CH_2$); m/z (CI+, $NH_3$) 239 (M+—$C_9H_{11}O$+H)

EXAMPLE 30

2-(3-Hydroxyphenyl)-1-ethyl 7-Chloro-2,4-dioxo-3-(1,2,3,4-tetrahydroquinoline)carboxylate White needles, m.p. 257°–259° C. (from dimethylformamide/acetone/water) (Found: C, 59.92; H, 3.99; N, 3.95. $C_{18}H_{14}NO_5Cl$ requires C, 60.09; H, 3.92; N, 3.89%); $\delta$($d_6$-DMSO) 13.3 (1H, br s), 11.58 (1H, s), 9.27 (1H, s), 7.93 (1H, d, J=8.7 Hz, H-5), 7.29 (1H, d, J=1.8 Hz, H-8), 7.24 (1H, dd, J=1.8 and 8.7 Hz, H-6), 7.08 (1H, t, J=7.8 Hz, CHCHCOH), 6.76 (1H, d, J=7.8 CHCHCHCOH), 6.71 (1H, d, J=1 Hz, CCHCOH), 6.62 (1H, dd, J=1 and 7.8 Hz, CHCHCOH), 4.44 (2H, t, J=7.2 Hz, $CH_2OCO$), 2.92 (2H, t, J=7.2 Hz, $CH_2Ar$); m/z (EI+) 359 (M+).

EXAMPLE 31

2-(5-Methoxy-3-indole)ethyl 7-Chloro-2,4-dioxo-3-(1,2,3,4-tetrahydroquinoline)carboxylate White plates m.p. 229°–231° C. (from dimethylformamide/acetone); (Found: C 60.27; H, 4.28; N, 7.22. $C_{21}H_{17}N_2O_5Cl$+0.3 dimethylformamide requires C, 60.50; H, 4.42; N, 7.41%); $\delta$($d_6$-DMSO) 13.3 (1H, br s), 11.62 (1H, s), 10.74 (1H, s), 7.93 (1H, d, J=8.6 Hz, H-5), 7.35–7.30 (2H, m, H-8 and indole H-2), 7.25 (1H, dd, J=2.0 and 8.6 Hz, H-6), 7.22 (1H, d, J=8.7 Hz, indole H-7), 7.08 (1H, d, J=2.2 Hz, indole H-4), 6.70 (1H, dd, J=2.0 and 8.7 Hz, indole H-6), 4.49 (2H, t, J=7 Hz, $OCH_2$), 3.74 (3H, s, Me), 3.10 (2H, t, J=7 Hz, $CH_2Ar$); m/z (EI+) 368 (M—$CO_2$).

EXAMPLE 32

3-(3-Methoxyphenyl)prop-2-ynyl 7-Chloro-3-(1,2,3,4-tetrahydroquinoline)carboxylate White needles m.p.>310° C. (from dimethylformamide/water); (Found: C, 61.99; H, 3.56; N, 3.93. $C_{20}H_{14}ClNO_5$+0.1 $H_2O$ requires C, 62.30; H, 3.71; N, 3.63%); $\delta$($d_6$ DMSO) 13.0 (1H, br s), 11.64 (1H, s), 7.95 (1H, d, J=8.6 Hz, H-5), 7.33–7.29 (2H, m, H-8 and OCCHCH), 7.25 (1H, dd, J=2.0 and 8.6 Hz, H-6), 7.06 (1H, d, J=7.6 Hz, CHCHCH), 7.02 (1H, d, J=2.2 Hz, OCCHC), 7.01 (1H, dd, J 8 ad 2.2 Hz, CHCHCH), 5.20 (2H, s, $CH_2$), 3.77 (3H, s, Me); m/z (CI+, $NH_3$) 239 (M+—$C_{10}H_9O$+H).

EXAMPLE 33

3-(3-Indole)-1-propyl 7-Chloro-2,4-dioxo-3-(1,2,3,4-tetrahydroquinoline)carboxylate Pale yellow solid m.p. 219°–220° C. (from dimethylformamide/acetone); (Found: C, 63.24; H, 4.07, N, 6.91. $C_{21}H_{17}N_2O_4Cl$ requires C, 63.56; 4.32; N, 7.06%); $\delta(d_6\text{-DMSO})$ 13.3 (1H, br s), 11.57 (1H, s), 10.76 (1H, s), 7.94 (1H, d, J=8.6 Hz, H-5), 7.56 (1H, d, J=7.9 Hz, indole H-4), 7.35–7.30 (2H, m, H-8 and indole H-7), 7.25 (1H, dd, J 1.8 and 8.6 Hz, H-6), 7.16 (1H, s, indole H-2), 7.05 (1H, t, J=7 Hz, indole H-5 or H-6), 6.95 (1H, t, J=7 Hz, indole H-6 or H-5), 4.32 (2H, t, J=7 Hz, $OCH_2$), 2.86 (2H, t, J=7 Hz $CH_2Ar$), 2.06 (2H, quin, J=7 Hz, $CH_2CH_2CH_2$); m/z ($CI^+$, $NH_3$) 239 ($M^+$—$C_{11}H_{12}N$+H).

EXAMPLE 34

2-[3,4-Bis(methoxymethoxy)phenyl]ethyl 7-Chloro-2,4-dioxo-3-(1,2,3,4-tetrahydroquinoline)carboxylate White cubes, m.p. 202°–204° C. (from dimethylformamide/acetone/water); (Found: C, 57.04; H, 4.81; N, 3.08. $C_{22}H_{22}NO_8Cl$ requires C, 56.96; H, 4.78; N, 3.02%); $\delta(d_6\text{-DMSO})$ 13.3 (1H, br s), 11.58 (1H, s), 7.93 (1H, d, J=8.6 Hz, H-5), 7.30 (1H, d, J=1.9 Hz, H-8), 7.24 (1H, dd, J=1.9 and 8.6 Hz, H-6), 7.13 (1H, d, J=1.9 Hz, OCCHC), 7.00 (1H, d, J=7.5 Hz, OCCHCH), 6.93 (1H, dd, J=1.9 and 7.5 Hz, OCCHCH), 5.17 (2H, s, $OCH_2O$), 5.13 (2H, s, $OCH_2O$), 4.43 (2H, t, J=7 Hz, $OCOCH_2$), 3.38 (3H, s, Me), 3.37 (3H, s, Me), 2.93 (2H, t, J=7 Hz, $CH_2Ar$); m/z ($CI^+$, $NH_3$) 464 ($M^+$+H).

EXAMPLE 35

4-(3-Hydroxyphenyl)-1-butyl 7-Chloro-3-)1,2,3,4-tetrahydroquinoline)carboxylate White lozenges, m.p. 187°–188° C. (from acetone); (Found: C, 62.15; H, 4.45; N, 3.59. $C_{20}H_{18}ClNO_5$ requires C, 61.94; H, 4.86; N, 3.61%); $\delta(d_6\text{-DMSO})$ 13.3 (1H, br s), 11.54 (1H, s), 9.19 (1H, s), 7.93 (1H, d, J=8.6Hz, H-5), 7.30 (1H, d, J=1.8Hz, H-8), 7.24 (1H, dd, J=1.8 and 8.6Hz, H-6), 7.05 (1H, t, J=7.7Hz, HOCCHCH), 6.62 (1H, d, J=7.7Hz, CHCHCH), 6.61 (1H, d, J=2.5Hz, HOCCHC), 6.56 (1H, dd, J=7.7 and 2.5Hz, CHCHCH), 4.30 (2H, br s, $OCH_2$), 2.55 (2H, br s, $CH_2Ar$), 1.69 (4H, br s, $CH_2CH_2CH_2CH_2$); m/z ($EI^+$) 387($M^+$).

EXAMPLE 36

3-(3-Hydroxyphenyl)-1-propyl 7-Chloro-2,4-dioxo-3-(1,2,3,4-tetrahydroquinoline)carboxylate White solid, m.p. 224°–226° C. (from dimethylformamide/acetone/water); (Found: C, 60.87; H, 4.25; N, 3.72. $C_{19}H_{16}NO_5Cl$ requires C, 61.05; N, 4.31; 3.74%); $\delta(d_6\text{-DMSO})$ 13.3 (1H, br s), 11.54 (1H, s), 9.2 (1H, br s), 7.93 (1H, d, J=8.6Hz, H-5), 7.31 (1H, d, J=1.9Hz, H-8), 7.24 (1H, dd, J= 1.9 and 8.6, H-6), 7.07 (1H, t, J=8Hz, HOCCHCH), [6.85–6.8 (2H, m) and 6.57 (1H, dd, J=1.7 and 8Hz), other ArH], 4.28 (2H, t, J=7Hz, $OCH_2$), 2.66 (2H, t, J=7Hz, $CH_2Ar$), 1.96 (2H, quin, J=7Hz, $CH_2CH_2CH_2$); m/z ($EI^+$) 373 ($M^+$).

EXAMPLE 37

2-(3-Indole)-ethyl 7-Chloro-2,4-dioxo-3-(1,2,3,4-tetrahydroquinoline)carboxylate White amorphous solid m.p. 233°–235° C. (from dimethylformamide); (Found: C, 62.62; H, 3.70; N, 7.17. $C_{20}H_{15}N_2O_4Cl$ requires C, 62.76; H, 3.95; N, 7.32%); $\delta(d_6\text{-DMSO})$ 13.4 (1H, br s), 11.58 (1H, s), 10.87 (1H, s), 7.93 (1H, d, J=8.6Hz, H-5), 7.60 (1H, d, J=7.8Hz, indole H-4), 7.4–7.3 (3H, m, H-8, indole H-2 and H-7), 7.24 (1H, dd, J=2.0 and 8.6Hz, H-6), 7.07 (1H, t, J=7Hz, indole H-5 or H-6), 6.98 (1H, t, J=7Hz, indole H-6 or H-5), 4.51 (2H, t, J=7Hz, $OCH_2$), 3.14 (2, t, J 7Hz, $CH_2Ar$); m/z ($CI^+$, $NH_3$) 239 ($M^+$-$C_{10}H_{10}N$+H).

EXAMPLE 38

3-(2-Hydroxyphenyl)-1-propyl 7-Chloro-2,4-dioxo-3-(1,2,3,4-tetrahydroquinoline)carboxylate White cubes m.p. 225°–227° C. (from dimethylformamide/acetone/water); (Found: C, 60.96; H, 4.28; N, 3.75. $C_{19}H_{16}NO_5Cl$ requires C, 61.05; H, 4.31; N, 3.75%); $\delta(d_6\text{-DMSO})$ 13.3 (1H, br s), 11.55 (1H, s), 9.26 (1H, br s), 7.93 (1H, d, J=8.7Hz, H-5), 7.30 (1H, d, J=1.96 H-8), 7.24 (1H, dd, J=1.9 and 8.7Hz, H-6), 7.09 (1H, dd, J=1.6 and 7Hz, $CH_2CCH$), 7.00 (1H, dt, J=1.6 and 7Hz, HOCCHCH), 6.78 (1H, dd, J=1 and 7Hz, HOCCH), 6.70 (1H, dt, J=1 and 7Hz, $CH_2CCHCH$), 4.26 (2H, t, J=7Hz, $OCH_2$), 2.67 (2H, t, J=7Hz, $CH_2Ar$), 1.96 (2H, quin, J=7Hz, $CH_2CH_2CH_2$); m/z ($CI^+$,$NH_3$) 374 ($M^+$+H).

EXAMPLE 39

2-[4-(Tert-butyloxycarbonylaminomethyl)phenyl]ethyl 7-Chloro-2,4-dioxo-3-(-1,2,3,4-tetrahydroquinoline)carboxylate White needles m.p. 239°–241° C. (from dimethylformamide); (Found: C, 60.72; H, 5.33; N, 5.95. $C_{24}H_{25}N_2O_6Cl$ requires C, 60.95; H, 5.33; N, 5.92%); $\delta(d_6\text{-DMSO})$ 13.3 (1H, br s), 11.56 (1H, s), 7.92 (1H, d, J=8.6Hz, H-5), 7.3–7.25 (4H, m, H-8, NH, ArH), 7.24 (1H, dd, J=2 and 8.6Hz, H-6), 7.15 (2H, d, J=8Hz, ArH), 4.44 (2H, t, J=7Hz, $OCH_2$), 4.08 (2H, d, J=5.7Hz, $NCH_2$), 2.98 (2H, t, J=7Hz, $CH_2Ar$), 1.38 (9H, s, $^tBu$); m/z ($CI^+$, $NH_3$) 473 ($M^+$+H).

EXAMPLE 40

1-(2-Propenyl) 7-Chloro-2,4-dioxo-3-(1,2,3,4-tetrahydroquinoline)carboxylate White needles m.p. >320° C. (from dimethylformamide); (Found: C, 55.79; H, 3.63; N, 5.00. $C_{13}H_{10}ClNO_4$ requires C, 55.83; H, 3.60; N, 5.01%); $\delta(d_6\text{-DMSO})$ 13.3 (1H, br s), 11.58 (1H, s), 7.94 (1H, dd, J=8.6Hz, H-5), 7.30 (1H, d, J 1.9Hz, H-8), 7.25 (1H, dd, J=1.9 and 8.6Hz, H-6), 6.06–5.96 (1H, m, $CHCH_2$), 5.57 (1H, d with other fine coupling, J=17Hz, C=$CH_AH_B$), 5.27 (1H, d with other fine coupling, J=9Hz, C=$CH_AH_B$), 4.83–4.81 (2H, m, $OCH_2$); m/z ($EI^+$) 279 ($M^+$).

EXAMPLE 41

2-(3-Thiophene)ethyl 7-Chloro-2,4-dioxo-3-(1,2,3,4-tetrahydroquinoline)carboxylate White needles m.p. 293° C. (sublimes) (from dimethylformamide/water); (Found: C, 54.79; H, 3.37; N, 4.08. $C_{16}H_{12}ClNO_4S$ requires C, 54.94; H, 3.46; N, 4.00%); $\delta(d_6$-DMSO) 13.3 (1H, br s), 11.59 (1H, s), 7.94 (1, d, J=8.7Hz, H-5), 7.45 (1H, dd, J=4.8 and 3.0Hz, SCHCH), 7.41 (1H, d, J=1.7Hz, SCHC), 7.30 (1H, d, J=1.9Hz, H-8), 7.25 (1H, dd, J=8.7 and 1.9Hz, H-6), 7.19 (1H, dd, J=4.8 and 1.1Hz, SCHCH), 4.46 (2H, t, J=6.7Hz, OCH$_2$), 3.04 (2H, t, J=6.7Hz, CH$_2$Ar); m/z (CI$^+$, NH$_3$) 350 (M$^+$+H).

EXAMPLE 42

2-(2-Thiophene)ethyl 7-Chloro-2,4-dioxo-3-(1,2,3,4-tetrahydroquinoline)carboxylate White needles m.p. 315° C. (dec) (from dimethylformamide/water); (Found: C, 55.02; H, 3.20; N, 4.07. $C_{16}H_{12}NO_4SCl$ requires C, 54.94; H, 3.46; N, 4.00%); $\delta(d_6$-DMSO) 13.2 (1H, br s), 11.57 (1H, br s), 7.94 (1H, d, J=8.6Hz, H-5), 7.35 (1H, dd, J=5.1 and 1Hz, SCH), 7.30 (1H, d, J=1.9Hz, H-8), 7.25 (1H, dd, J=1.9 and 8.6Hz, H-6), 7.07 (1H, dd, J=3.4 and 1Hz, SCHCHCH), 6.96 (1H, dd, J=5.1 and 3.4Hz, SCHCH), 4.47 (2H, t, J=6.8Hz, OCH$_2$), 3.23 (2H, t, J=6.8Hz, CH$_2$Ar); m/z (CI$^+$, NH$_3$) 350 (M$^+$+H).

EXAMPLE 43

2-(4-Hydroxyphenyl)-1-ethyl 7-Chloro-2,4-dioxo-3-(1,2,3,4-tetrahydroquinoline)carboxylate White needles m.p. 258°-260° C. (from dimethylformamide/acetone); (Found: C, 59.72; H, 4.02; N, 4.02. $C_{18}H_{14}NO_5Cl$ requires C, 60.09; H, 3.92; N, 3.89%); $\delta(d_6$-DMSO) 13.3 (1H, br s), 11.59 (1H, s), 9.19 (1H, s), 7.93 (1H, d, J=8.7Hz, H-5), 7.29 (1H, d, J=1.9Hz, H-8), 7.24 (1H, dd, J=1.9 ad 8.7Hz, H-6), 7.14 (2H, d, J=8.4Hz, CH$_2$CCH), 6.67 (2H, d, J=8.4Hz, HOCCH), 4.39 (2H, t, J=7.1Hz, OCH$_2$), 2.89 (1H, t, J=7.1Hz, CH$_2$Ar); m/z (FAB$^-$) 358 (M$^+$-H).

EXAMPLE 44

2-(2-Hydroxyphenyl)-1-ethyl 7-Chloro-2,4-dioxo-3-(1,2,3,4-tetrahydroquinoline)carboxylate White needles m.p.>320° C. (from dimethylformamide/acetone/water); (Found: C, 59.91; H, 3.95; N, 3.91. $C_{18}H_{14}NO_5Cl$ requires C, 60.09; H, 3.92; N, 3.89%); $\delta(d_6$-DMSO) 13.3 (1H, br s), 11.58 (1H, s), 9.45 (1H, br s), 7.93 (1H, d, J=8.6Hz, H-5), 7.29 (1H, d, J=1.9Hz, H-8), 7.24 (1H, dd, J=1.9 and 8.6Hz, H-6), 7.18 (1H, dd, J=1.5 and 8Hz, CH$_2$CH), 7.04 (1H, dt, J=1.5 and 8Hz, HOCCHCH), 6.80 (1H, d, J=8Hz, HOCCH) 6.71 (1H, t, J=8Hz, CH$_2$CCHCH), 4.43 (2H, t, J=7.4Hz, OCH$_2$), 2.96 (2H, t, J=7.4Hz, CH$_2$Ar); m/z (EI$^+$) 359 (M$^+$).

EXAMPLE 45

3-(3-Hydroxyphenyl)prop-2-ynyl 7-Chloro-2,4-dioxo-3-(1,2,3,4-tetrahydroquinoline)carboxylate Off-white crystalline solid, m.p. 234°-236° C. (from dimethylformamide/acetone/water); (Found: C, 61.34; H, 3.07; N, 3.61. $C_{19}H_{15}ClNO_5$. 0.1 H$_2$O requires C, 61.42; H, 3.31; N, 3.77%); $\delta(d_6$-DMSO) 13.0 (1H, v. br s), 11.65 (1H, br s), 9.69 (1H, br s), 7.95 (1H, d, J=8.6Hz, H-5), 7.3 (1H, d, J=7.8Hz, H-8), 7.26 (1H, dd, J=8.6 and 1.9Hz, H-6), 7.19 (1H, t, J=7.8Hz, CHCHCH), 6.90 (1H, d, J=7.8Hz, CHCHCH), 6.83 (1H, s, C(OH) CHC), 6.82 (1H, d, J=7.8Hz, CHCHCH), 5.18 (2H, s, CH$_2$); m/z (CI$^+$, NH$_3$) 239 (M—CH$_2$CCAr).

EXAMPLE 46

(E)-(3-Methoxyphenyl)prop-2-enyl 7-Chloro-2,4-dioxo-3-(1,2,3,4-tetrahydroquinoline)carboxylate Fine white needles, m.p.=181°-183° C. (from dimethyl formamide/acetone); (Found: C, 62.07; H, 4.07; N, 3.64. $C_{20}H_{16}ClNO_5$ requires C, 62.26; H, 4.18; N, 3.63%); $\delta(d_6$-DMSO) 13.3 (1H, v, br s), 11.61 (1H, br s), 7.95 (1H, d, J=8.6 Hz, H-5), 7.30 (1H, d, J=1.8 Hz, H-8), 7.30-7.27 (1H, Ar—H), 7.25 (1H, dd, J=8.6 and 1.8 Hz, H-6), 7.06-7.03 (2H, m, 2×Ar—H), 6.88-6.85 (1H, m, Ar—H), 6.82 (1H, d, J=16.1 Hz, Ar CH), 6.48 (1H, dt, J=16.1 and 6.0 Hz, CH$_2$CH), 4.98 (2H, d, J=6.0 Hz, CH$_2$), 3.77 (3H, s, OCH$_3$); m/z (EI$^+$), 341 (M-CO$_2$).

EXAMPLE 47

2-Phenylthioethyl 7-Chloro-2,4-dioxo-(1,2,3,4-tetrahydroquinoline)carboxylate

Fine white needles, m.p. 206°-208° C. (from dimethylformamide); (Found: C, 57.34; H, 3.51; N, 3.73. $C_{18}H_{14}NSO_4Cl$ requires C, 57.53; H, 3.75; N, 3.73%); $\delta(d_6$-DMSO) 13.0 (1H, br s), 11.57 (1H, s), 7.93 (1H, d, J=8.6 Hz, H-5), 7.43 (2H, dd, J=7.5 and 1.4 Hz, SCCH), 7.29 (2H, t, J=7.5 Hz, SCCHCH), 7.26 (1H, d, J=1.6 Hz, H-8), 7.21 (1H, dd, J=8.6 and 1.6 Hz, H-6), 7.19 (1H, dt, J=1.4 and 7.5 Hz, SCCHCHCH), 4.42 (2H, t, J=7.2 Hz, OCH$_2$), 3.3 (2H, t, J=7.2 Hz, SCH$_2$); m/z (CI$^-$, NH$_3$), 374 (M$^+$-H).

EXAMPLE 48

S-2-Phenylethyl 7-Chloro-2,4-dioxo-3-(1,2,3,4-tetrahydroquinoline)thiocarboxylate Using phenyethyl mercaptan to give pale yellow needles, m.p. >320° C. (from dimethyl formamide/acetone/water), change of crystalline form at 237°-241° C.; (Found: C, 60.25; H, 3.73; N, 3.97. $C_{18}H_{14}CLNO_3S$ requires C, 60.08; H, 3.92; N, 3.89%), $\delta(d_6$-DMSO) 15.0 (1H, v br s), 11.82 (1H, br s), 8.00 (1H, d, J=8.6 Hz, H-5), 7.34-7.22 (7H, m, H-6, H-8, 5×Ar), 3.19 (2H, t, J=7.6 Hz, SCH$_2$), 2.91 (2H, t, J=7.6 Hz, CH$_2$ Ph); m/z (EI$^+$) 255 (M-C$_6$H$_5$CH$_2$CH$_2$+H).

EXAMPLE 49

Ethyl 7-Nitro-2,4-dioxo-3-(1,2,3,4-tetrahydroquinoline)carboxylate

Ethyl malonyl chloride (3.15 g) in dry dichloromethane (10 ml) was added dropwise to a stirred solution of ethyl-4-nitroanthranilate (2.01 g), triethylamine (4.7 ml) and 4-dimethylaminopyridine (0.080 g) in dry dichloromethane (10 ml) at 0° C. under $N_2$. After complete addition the reaction was maintained at 0° C. for 45 min before further triethylamine (4.7 ml) was introduced, followed by dropwise addition of ethyl malonyl chloride (3.15 g) in dry dichloromethane (10 ml). The reaction was stirred at 0° C. for 45 min. The suspension was concentrated in vacuo, diluted with ethyl acetate, washed twice with 10% citric acid followed by saturated sodium hydrogen carbonate solution, water and brine. The organics were dried ($MgSO_4$) and concentrated in vacuo to give a deep orange oil (2.51 g). The oil was dissolved in ethanol (15 ml) and a solution of sodium methoxide (0.84 g) in ethanol (15 ml) added with vigorous stirring. After 1 hour the mixture was diluted with ethyl acetate and extracted three times with 1N sodium hydroxide solution. The combined aqueous fractions were acidified to pH 0 with 2N hydrochloric acid and the resulting precipitate filtered off, washed with water and dried in vacuo over phosphorus pentoxide to give 1.3 g of a deep yellow solid. This solid was washed with boiling ethanol and dried to yield the ester (0.637 g) as fine light yellow crystals, m.p. >325° C. (Found: C, 51.56; H, 3.59; N, 9.98. $C_{12}H_{10}N_2O_6$ requires C, 51.81; H, 3.62; N, 10.07%); $\delta$(D$_6$-DMSO) 11.89 (1H, br s), 8.16 (1H, d, J 8.8 Hz, H-5), 8.10 (1H, d, J=2.2 Hz, H-8), 7.96 (1H, dd, J=2.2 and 8.8 Hz, H-6), 4.33 (2H, q, J=7.1 Hz, $CH_2$), 1.30 (3H, t, J=7.1 Hz, $CH_3$), m/z (EI$^+$) 278 (M$^+$).

EXAMPLE 50

Ethyl 6,7-Dinitro-2,4-dioxo-3-(1,2,3,4-tetrahydroquinoline)-carboxylate

A 1:1 mixture of concentrated sulphuric and concentrated nitric acids (0.5 ml:0.5 ml) was added dropwise to a cooled (ice bath) stirred suspension of ethyl 7-nitro-2,4-dioxo-3-(1,2,3,4-tetrahydroquinoline)carboxylate (0.139 g) in concentrated sulphuric acid (2 ml) under $N_2$. The reaction was warmed to 60° C. for 45 min, then cooled to room temperature and diluted with cold distilled water. The resulting precipitate was filtered off, washed with water and dried in vacuo to give the ester (0.055 g) as fine cream coloured crystals, m.p. 229°–230° C. (from ethanol); (Found: C, 44.44; H, 2.78; N, 12.86. $C_{12}H_9N_3O_8$ requires C, 44.59; H, 2.81; N, 13.00%); $\delta$(d$_6$-DMSO) 12.37 (1H, br s), 8.68 (1H, s, H-5), 7.80 (1H, s, H-8), 4.31 (2H, q, J=7.1 Hz, $CH_2$), 1.29 (3H, t, J=7.1 Hz, $CH_3$); m/z (EI$^+$) 323 (M$^+$).

EXAMPLE 51

Ethyl 7-Chloro-2,4-dioxo-5-iodo-3-(1,2,3,4-tetrahydroquinoline carboxylate

A mixture of 3-chloro-5-iodoaniline (63.41 g) in water (150 ml), concentrated hydrochloric acid (22.1 ml) and 1,4-dioxan (~60 ml) was heated to gain solution before being added to a mixture of chloral hydrate (90.24 g) and sodium sulphate (650 g) in water (600 ml) which had been warmed to 50° C., Hydroxylamine hydrochloride (110.56 g) in water (250 ml) was then added and the reaction heated at reflux for 45 mins before being allowed to cool to room temperature and the resultant yellow precipitate of 3-chloro-5-iodophenylisonitrosoacetanilide filtered off, washed with water and dried in vacuo over silica gel.

A sample of the isonitrosoacetanilide (45 g) was added portionwise to pre-warmed concentrated sulphuric acid (175 ml, 50° C.) keeping the internal temperature between 50° C. and 70° C., using an ice bath. After complete addition, the now dark solution was heated at 80° C. for 10 minutes before being allowed to cool to room temperature and poured on to ten times the reaction volume of ice. The resultant slurry was swirled vigorously and left to stand for one hour before filtering off the resultant rust coloured precipitate, washing with water and drying in vacuo over phosphorus pentoxide. This yielded a mixture of 6-chloro-4-iodo and 4-chloro-6-iodo isatins. $\delta$ (d$_6$-DMSO), 11.26 (1H, s, N'H), 11.18 (1H, s, NH), 7.55 (1H, d, J=1.6 Hz, H-5 or H-7), 7.50 (1H, d, J=1.0 Hz, H-5' or H-7'), 7.25 (1H, d, J=1.0 Hz, H-5' or H-7'), 6.98 (1H, d, J=1.6 Hz, H-5 or H-7).

30% hydrogen peroxide (35.7 ml) was added portionwise to a solution of the mixture above isatins (53.68 g) at room temperature in 1N sodium hydroxide solution (525 ml). Once effervescence had stopped, the reaction was cautiously neutralized with 2N hydrochloric acid and filtered to remove insolubles before acidifying to pH 2-3. The resultant sandy yellow precipitate was filtered off and washed with water before drying in vacuo over phosphorus pentoxide to yield a mixture of the 2-amino-4-chloro-6-iodo and 2-amino-6-chloro-4-iodo benzoic acids (10.56 g). Dissolving the mixture of isomers (8 g) in boiling acetone and reducing the volume until a solid started to crystallise out, resulted in the formation of the Schiff's base (enriched (10:1) in the more prevalent 4-chloro-6-iodo isomer). Hydrolysis of this imine with 2N hydrochloric acid yielded the amino benzoic acid. Repetition of this process gave the 2-amino-4-chloro-6-iodo benzoic acid (3.75 g) in >95% purity. $\delta$ (d$_6$-DMSO) 7.05 (1H, d, J=1.9 Hz, H-3 or H-5), 6.79 (1H, d, J=1.9 Hz, H-3 or H-5).

Treatment of an ethereal solution of the acid (2.68 g) with diazomethane and concentration in vacuo, yielded the desired methyl 2-amino-4-chloro-6-iodobenzoate (2.81 g) as a yellow oil which crystallised on standing. $\delta$ (d$_6$-DMSO) 7.04 (1H, d, J=1.9 Hz, H-3 or H-5), 6.78 (1H, d, J=1.9 Hz, H-3 or H-5), 5.89 (2H, s, $NH_2$), 3.61 (3H, s, $CH_3$).

Addition under nitrogen at room temperature of a solution of ethyl malonyl chloride (2.03 g) in dry dichloromethane (15 ml) to a solution of the benzoate (2.81 g) in dry dichloromethane (15 ml), resulted in the rapid formation of a gelatinous white precipitate. The solvent was removed in vacuo and the precipitate triturated with diethyl ether to leave the methyl 2-malonamido-4-chloro-6-iodo benzoate as an off white solid (2.33 g).

Cyclisation of the methyl 2-malonamido-4-chloro-6-iodo benzoate was achieved by addition of a solution of sodium methoxide (0.25 g) in ethanol (10 ml) under nitrogen, to a vigorously stirred solution of the benzoate (1.83 g) in ethanol (15 ml) at room temperature. After 1¼ hours the reaction was diluted with ethyl acetate and extracted three times with 1N sodium hydroxide. The combined aqueous fractions were acidified to pH 1 with 2N hydrochloric acid and the resultant white precipitate filtered off and washed with water, before being crystallised from hot DMF (keeping the solvent temperature ≦80° C.). This gave the title compound as very fine needle crystals (0.571 g), melting point 212°–216° C.; (Found: C, 36.48; H, 2.09; N, 3.49. $C_{12}H_9ClIN O_4$ requires C, 36.62; H, 2.31; N, 3.56%); δ(d$_6$-DMSO) 11.65 (1H, s), 7.86 (1H, d, J=2.0 Hz, H-6 or H-8), 7.33 (1H, d, J=2.0 Hz, H-6 or H-8), 4.35 (2H, q, J=7.1 Hz, CH$_2$CH$_3$), 1.31 (3H, t, J=7.1 Hz, CH$_2$CH$_3$); m/z (EI+) 393 (M+).

EXAMPLE 52

2-(3-Indole)-1-ethyl 7-Chloro-2,4-dioxo-5-iodo-3-(1,2,3,4-tetrahydroquinoline) carboxylate Tryptophol (0.68 g) and ethyl 7-chloro-2,4-dioxo-5-iodo-3-(1,2,3,4-tetrahydroquinoline) carboxylate (0.160 g) were mixed together as a slurry in diethyl ether and the solvent removed in vacuo to leave the reactants as a finely blended residue. This was then heated under nitrogen at 150° C. for 40 mins before introducing a further 0.65 g of tryptophol and heating at 150° C. for 25 mins. The reaction was allowed to cool to room temperature before washing with diethyl ether. The resultant white solid was crystallised from DMF to give the title compound as fine white crystals (0.109 g), melting point 240°–244° C.-decomposes; (Found: C, 47.05; H, 2.63; N, 5.40. $C_{20}H_{14}ClIN_2O_4$ requires C, 47.22; H, 2.77; N, 5.51%); δ(d$_6$-DMSO) 11.67 (1H, s), 10.87 (1H, s), 7.87 (1H, d, J=2.1 Hz, H-6 or H-8), 7.60 (1H, d, J=7.1 Hz, indole H-4 or indole H-7), 7.33 (3H, m, H-6 or H-8, and indole H-2, and indole H-4 or indole H-7), 7.06 (1H, t, J=7.1 Hz, indole H-5 or indole H-6), 6.98 (1H, t, J=7.0 Hz, indole H-5 or indole H-6), 4.52 (2H, t, J=7.2 Hz, CH$_2$OCOR), 3.14 (2H, t, J=7.2 Hz, CH$_2$-indole); m/z (CI+) 365 ((M-C$_{10}$H$_{10}$N+H)+).

Methyl 4-Chloro-6-vinylanthranilate

Vinyltributyltin (1.6 ml), lithium chloride (dried at 100° C. under vacuum for 18 h) (780 g) and bis triphenylphosphine palladium (II) dichloride (265 mg) were added to a stirred solution of methyl 4-chloro-6-iodoanthranilate (1.63 g) in dry dimethyl formamide (20 ml) at room temperature. The mixture was heated under nitrogen at 60° C. for 40 mins. After cooling, the solution was diluted with ethyl acetate (125 ml), washed with water (3×100 ml) and brine, dried (Na$_2$SO$_4$) and evaporated in vacuo to give an oil. This was purified by flash chromatography eluting with ethylacetate/hexane to give the anthranilate as an off-white crystalline solid (1.02 g); δ(d$_6$-DMSO) 6.83 (1H, dd, J=17.3 Hz and 11.0 Hz, ArCH), 6.75–6.73 (2H, m, H-3 and H-5), 6.01 (2H, br s, NH$_2$), 5.65 (1H, dd, J=17.3 Hz and 1.1 Hz, CH$_A$H$_B$, H$_A$ cis to Ar), 5.26 (1H, dd, J=11.0 Hz and 1.1 Hz, CH$_A$H$_B$, H$_B$ trans to Ar), 3.80 (3H, s, CH$_3$).

Methyl 4-Chloro-6-ethylanthranilate

5% platinum on sulphide carbon (300 mg) was added to a solution of methyl 4-chloro-6-vinylanthranilate (1.01 g) in ethyl acetate (80 ml). The suspension was hydrogenated at 50 p.s.i. for 2 h. The catalyst was removed by filtration and the solution evaporated in vacuo to give the anthranilate as a clear colourless oil (1.02 g); δ(d$_6$-DMSO) 6.65 (1H, d, J=2.5 Hz, H-3 or H-5), 6.46 (1H, d, J=2.5 Hz, H-3 or H-5), 5.85 (2H, br s, NH$_2$), 3.81 (3H, s, OCH$_3$), 2.60 (2H, q, J=7.5 Hz, CH$_2$), 1.08 (3H, t, J=7.5 Hz, CH$_2$CH$_3$).

EXAMPLE 53

Methyl 7-Chloro-5-ethyl-2,4-dioxo-3-(1,2,3,4-tetrahydroquinoline)carboxylate

Methyl malonyl chloride (140 μl) was added to a solution of methyl 4-chloro-6-ethaylanthranilate (250 mg) in dry dichloromethane (10 ml). The mixture was heated at reflux under nitrogen to redissolve the precipitate. After 2 h, the solution was cooled and evaporated in vacuo. The residue was diluted with ethyl acetate, washed with 0.5N citric acid, saturated sodium bicarbonate solution and brine, dried (Na$_2$SO$_4$) and reduced in vacuo to give a clear colourless oil (340 mg). 300 mg of this oil was dissolved in dry methanol (10 ml) then sodium methoxide (90 mg) was added. After 1 h the suspension was evaporated in vacuo and the residue partitioned between 1N sodium hydroxide solution and ether. The aqueous layer was acidified with concentrated hydrochloric acid and the resulting precipitate extracted into ethyl acetate (2×75 ml). The combined organic extracts were washed with water and brine, dried (Na$_2$SO$_4$) and evaporated to give an off-white solid. This solid was recrystallised from dimethyl formamide and water keeping the temperature below 90° C., then washed with water, acetone and ether and dried to give the ester as fine white rhombic crystals. m.p.>320° C. change of crystalline form at 197°–198° C.; (Found: C, 55.22; H, 4.22; N, 4.78. $C_{13}H_{12}ClNO_4$ requires C, 55.43; H, 4.29; N, 4.97%). δ(d$_6$-DMSO) 14.5 (1H, v br s), 11.54 (1H, br s), 7.17 (1H, d, J=2.0 Hz, H-6 or H-8), 7.05 (1H, d, J=2.0 Hz, H-6 or H-8), 3.88 (3H, s, OCH$_3$, 3.12 (2H, q, J=7.3 Hz, CH$_2$), 1.20 (3H, t, J=7.3 Hz, CH$_2$CH$_3$).

EXAMPLE 54

7-Chloro-3-(3-methyl-1,2,4-oxadiazol-5-yl)-2,4-dioxo-1,2,3,4-tetrahydroquinoline Ethyl-7-chloro-2,4-dioxo-3-(1,2,3,4-tetrahydroquinoline)carboxylate (0.40 g) and acetamide oxime (1.1 g) were heated at 130° C. in dimethylformamide (10 ml) for 4 h. The mixture was cooled, water (25 ml) and 1M hydrochloric acid (2 ml) were added, and the solid collected, washed with water and ethanol, dried and recrystallised from dimethylsulphoxide to give the tetrahydroquinoline (107 mg) as a tan solid, m.p.>320° C., (Found: C, 51.09; H, 3.06; N, 14.61. $C_{12}H_8N_3O_3Cl+0.3 H_2O$ requires C, 50.92; H, 3.06; N, 14.84%); δ(d$_6$-DMSO) 11.68 (1H, s), 7.99 (1H, d, J=8.6 Hz, H-5), 7.32 (1H, d, J=1.8 H-8), 7.28 (1H, dd, J=1.8 ad 8.6 Hz, H-6), 2.46 (3H, s, Me); m/z (EI+) 277 (M+).

EXAMPLE 55

(E) Ethyl 3-(7-Chloro-2,4-dioxo-(1,2,3,4-tetrahydroquinolin-3-yl)-2-propenoate

Sodium hydroxide (13 ml of a 4N aqueous solution) was added to diethylglutaconate (10 g) in ethanol (100 ml). After 14 h the mixture was diluted with water, washed with ether, acidified and extracted with ether (3×50 ml). The combined organic layers were washed with water and brine, dried, and evaporated to give an oil (5.1 g). Oxalyl chloride (1.34 ml) was added to a solution of 1.21 g of this oil in dry dichloromethane (18 ml) and dimethylformamide (1 drop). After 2 h the mixture was evaporated, dissolved in dichloromethane (7 ml) and added to a solution of ethyl 4-chloroanthranilate (0.4 g), triethylamine (1.4 ml) and 4-dimethylaminopyridine (100 mg) in dichloromethane (20 ml) at 0° C. The mixture was stirred at 0° C. for 1 h, room temperature for 1 h, diluted with ethyl acetate, washed with 1M citric acid, sodium hydroxide solution, and brine, dried, evaporated and purified by flash chromatography, eluting with hexanes:ethyl acetate, (4:1 v/v) to give the acylated anthranilate as a mixture of isomers (247 mg). This was dissolved in ethanol (10 ml) and sodium methoxide (0.05 g) added. After 1 h the mixture was poured into 0.2M HCl (25 ml) the product collected, washed with water, dried, suspended in boiling ethanol (100 ml), cooled, the solid collected, washed with ethanol, dried to give the ester (64 mg) as white needles, m.p. 246°-249° C.; (Found: C, 57.11; H, 4.20; N, 4.71. $C_{14}H_{12}NO_4Cl$ requires C, 57.25; H, 4.12; N, 4.77%); $\delta(d_6\text{-DMSO})$ 11.62 (1H, s), 8.04 (1H, d, J=8.7 Hz, H-5), 7.98 (1H, d, J=15.8 Hz, CHCHCO), 7.51 (1H, d, J=2.0 Hz, H-8), 7.26 (1H, d, J=15.8 Hz, CHCHCO), 7.24 (1H, dd, J=2.0 and 8.7 Hz, H-6), 4.16 (2H, q, J=7.1 Hz, OCH$_2$), 1.25 (3H, t, J=7.1 Hz, CH$_3$); m/z (EI+) 293 (M+).

EXAMPLE 56

7-Chloro-2,4-dioxo-3-(1,2,3,4-tetrahydroquinoline)carboxylic acid

Sodium hydride (0.8 g of an 80% dispersion in oil) was added to a mixture of ethyl 7-chloro-2,4-dioxo-3-(1,2,3,4-tetrahydroquinoline)carboxylate (0.4 g) and 4-methoxyphenol (0.20 g) in dry dimethylformamide (5 ml) under nitrogen. After heating at 80° C. for 45 min the mixture was cooled, then water and dilute hydrochloric acid added. The resulting acid (0.21 g) was collected as a light tan solid, m.p.>310° C. (from acetone); (Found: C, 49.98; H, 2.41; H, 5.72. $C_{10}H_6NO_4Cl$ requires C, 50.13; H, 2.52; N, 5.85); $\nu$(KBr disc) 3300-2500 cm$^{-1}$; $\delta(d_6\text{-DMSO})$ 8.05 (1H, d, J=8.6 Hz, H-5), 7.48 (1H, d, J=1.7 Hz, H-8), 7.45 (1H, dd, J=1.7 and 8.6 Hz, H-6); m/z m/z (EI+) 239 (M+). This compound is unstable with respect to decarboxylation on heating.

The following compounds were made in the same general way (Method E): The desired ester and the corresponding amine were refluxed in dry pyridine for 2 h. On cooling and addition of dilute hydrochloric acid the product precipitated and was collected, washed with hydrochloride acid and ester, then dried.

EXAMPLE 57

7-Chloro-2,4-dioxo-3-(1,2,3,4-tetrahydroquinoline)hydroxamic acid

From methyl 7-chloro-2,4-dioxo-3-(1,2,3,4-tetrahydroquinoline)carboxylate (0.44 g) and hydroxylamine hydrochloride (2 g) as fine white needles (0.14 g), m.p. 280° C. (dec); (Found: C, 47.32; H, 2.59; N, 10.91. $C_{10}H_7N_2O_4Cl$ requires C, 47.17; H, 2.77; N, 11.00%); $\delta(d_6\text{-DMSO})$ 18 (1H, br s), 11.9 (1H, br s), 11.8 (1H, br s), 9.8 (1H, br s), 7.96 (1H, d, J=8.6 Hz, H-5), 7.38 (1H, d, J=1.8 Hz, H-8), 7.32 (1H, dd, J=1.8 and 8.6 Hz, H-6); m/z (CI+, NH$_3$) 255 (M++H).

EXAMPLES 58

7-Chloro-5-iodo-2,4-dioxo-3-(1,2,3,4-tetrahydroquinoline)hydroxamic acid

Ethyl 7-chloro-5-iodo-2,4-dioxo-3-(1,2,3,4-tetrahydroquinoline)carboxylate (0.2 g) and hydroxylamine hydrochloride (1.1 g) gave the acid (0.14 g) as white needles, m.p. 295° C. (dec); (Found C, 31.48; H, 1.45; N, 7.15. $C_{10}H_6N_2O_4ClI$ requires C, 31.56; H, 1.59; N, 7.36); $\delta(d_6\text{-DMSO})$ 18 (1H, br s), 12.0 (2H, br s), 9.9 (1H, br s), 7.90 (1H, d, J=2 Hz, H-8), 7.40 (1H, d, J=2 Hz, H-6); m/z (EI+) 380 (M+).

EXAMPLE 59

7-Chloro-2,4-dioxo-3-(1,2,3,4-tetrahydroquinoline)carboxylic acid hydrazide

From methyl 7-chloro-2,4-dioxo-3-(1,2,3,4-tetrahydroquinoline) (0.4 g) and hydrazine hydrate (2 g) as fine white needles (0.23 g), m.p. 288° C. (dec); (Found: C, 46.96; H, 3.11; N, 16.40. $C_{10}H_8N_3O_3Cl+0.05$ H$_2$O requires C, 47.19; H, 3.21; N, 16.51%); $\delta(d_6\text{-DMSO})$ 12 (4H, br s), 11 (1H, br s), 7.96 (1H, d, J=8.6 Hz, H-5), 7.40 (1H, d, J=1.8 Hz, H-8), 7.33 (1H, dd, J=8.6 and 1.8 Hz, H-6); m/z (EI+) 253 (M+).

EXAMPLE 60

7-Chloro-2,4-dioxo-3-(3-thienyl)-1,2,3,4-tetrahydroquinoline

To a solution of thiophene-3-acetic acid (1.4 g, 10 mmol) in dichloromethane (40 ml) was added oxalyl chloride (1.74 ml, 20 mmol) and dimethylformamide (catalytic, 3 drops) and the reaction stirred for 1 h. The solvent was evaporated and the residue co-evaporated with toluene (3×20 ml). The resulting acid chloride was dissolved in 1,2-dichloroethane (40 ml), methyl 2-amino-4-chlorobenzoate (1.5 g, 8 mmol) added and the reaction refluxed for 2 h. The residue remaining on evaporation of the solvent was triturated with diethyl ether to afford methyl 4-chloro-2-(3-thienyl)acetamidobenzoate as a tan solid (1 g), m.p. 96°-97° C. To a solution of the foregoing amide (0.5 g, 1.6 mmol) in tetrahydrofuran (25 ml) was added a solution of potassium hexamethyldisilazide in toluene (0.5M, 4 mmol) and the reaction stirred for 2 h. Methanol (5 ml) was added and the solvent evaporated. The residue was partitioned between aqueous sodium hydroxide (1M, 20 ml) and diethyl ether (20 ml), and the aqueous layer acidified with hydrochloric acid (5M). The resultant precipitate was collected and recrystallised from dimethylformamide/water to afford the title compound as a white solid; m.p. 341°-344° C. (from DMF/H$_2$O) (Found: C, 55.07; H, 2.86; Cl, 12.94; N, 5.16; S, 11.42; $C_{13}H_8ClNO_2S$, 0.5 H$_2$O requires C, 55.32; H, 3.03; Cl, 12.56; N, 4.96; S, 11.36%); $\delta$(DMSO-d$_6$) 7.22 (1H, dd, J=8.6 and 2 Hz, 6-H), 7.31 (1H, s, 8-H), 7.43 (1H, d, J=4.9 Hz, 5'-H), 7.49-7.51 (1H, m, 4'-H), 7.76 (1H, s, 2'-H), 7.98 (1H, d, J=8.6 Hz, 5-H), 11.55 (1H, s, NH); m/z 277 (M+).

The following compounds were made by the same method (Method F), typified by Example 60 above.

EXAMPLE 61

7-Chloro-2,4-dioxo-3-(2-thienyl)-1,2,3,4-tetrahydroquinoline m.p. 305°-307° C. (from DMF/H$_2$O) (Found: C, 55.32; H, 2.96; N, 5.09; S, 11.17; $C_{13}H_8ClNO_2S$, 0.25 H$_2$O requires C, 55.32; H, 3.04; N, 4.96;, S, 11.36%); $\delta$(DMSO-d$_6$) 7.11 (1H, dd, J=5.1 and 3.8 Hz, Th-H), 7.26 (1H, dd, J=8.8 and 2.1 Hz, 6-H), 7.35 (1H, d, J=2 Hz, 8-H), 7.50 (1H, dd, J=5.1 and 1.1 Hz, Th-H), 8.07 (2H, m, 5-H, Th-H), 11.73 (1H, s, NH); m/z 277 (M+).

EXAMPLE 62

7-Chloro-2,4-dioxo-3-(2-pyridyl)-1,2,3,4-tetrahydroquinoline

To a solution of methyl 2-amino-4-chlorobenzoate (2 g, 10.8 mmol) in 1,2-dichlorethane (60 ml) was added 2-pyridylacetic acid hydrochloride (1.9 g, 10.8 mmol), triethylamine (3.2 ml, 22.7 mmol) and bis (2-oxo-3-oxazolidinyl)phosphinic chloride and the reaction refluxed for 8 h. More 2-pyridylacetic acid (1.9 g, 10.8 mmol) and triethylamine (3.2 ml, 22.7 mmol) were added and refluxing continued for a further 16 h. The solvent was evaporated and the residue partitioned between saturated aqueous sodium bicarbonate solution (50 ml) and dichloromethane (50 ml). The organic phase was dried ($MgSO_4$) and evaporated. The residue was purified by flash chromatography on silica (eluting with 50% ethyl acetate/60°–90° petrol) to afford methyl 4-chloro-2-(3-pyridyl)acetamidobenzoate as a green solid (2.5 g), m.p. 85°–87° C. To a solution of the foregoing amide (1 g, 3.3 mmol) in tetrahydrofuran (40 mml) was added a solution of potassium hexamethyldisilazide in toluene (0.5M, 16.6 ml, 8.3 mmol) and the reaction stirred for 2 h. Methanol (15 ml) was added and the solvent evaporated. The residue was partitioned between aqueous sodium hydroxide (1M, 40 ml) and diethyl ether (40 ml), and the aqueous layer acidified with hydrochloric acid (5M). The resultant precipitate was collected and recrystallised from dimethylformamide/water to afford the title compound as a yellow-green solid; m.p.>330° C. (from $DMF/H_2O$) (Found: C, 61.48; H, 3.20; N, 10.20; $C_{14}H_9ClN_2O_2$ requires C, 61.66; H, 3.33; N, 10.27%); $\delta_H$(DMSO-d$_6$) 7.15 (1H, dd, J=8.5 Hz and 1.9 Hz, 5-H), 7.26 (1H, s, 8-H), 7.42 (1H, t, J=6.1 Hz, 5'-H), 8.02 (1H, d, J=8.5 Hz, 5-H), 8.16 (1H, t, J=7.3 Hz, 4'-H), 8.78 (1H, d, J=8.6 Hz, 6'-H), 9.38 (1H, d, J=8.8 Hz, 3'-H), 11.20 (1H, s, NH); m/z 272 (M+).

The following compounds were made by the same general method (Method G), typified by Example 62 above.

EXAMPLE 63

7-Chloro-2,4-dioxo-3-(3-pyridyl)-1,2,3,4-tetrahydroquinoline m.p.>340° C. (from $DMF/H_2O$) (Found: C, 61.23; H, 3.33; N, 10.23; $C_{14}H_9ClN_2O_2$, 0.05 $H_2O$ requires C, 61.46; H, 3.35, N, 10.24%); $\delta_H$(DMSO-d$_6$) 7.21 (1H, dd, J=8.5 and 1.9 Hz, 6-H), 1H, s, 8-H), 7.42–7.46 (1H, m, 5'-H), 7.90–8.48 (1H, m, 5-H, 6'-H), 8.48 (1H, s, 4'-H), 8.86 (1H, s, 2'-H), 11.52 (1H, s, NH); m/z 272 (M+).

EXAMPLE 64

7-Chloro-2,4-dioxo-3-(4-pyridyl)-1,2,3,4-tetrahydroquinoline m.p.>330° C. (from $DMF/H_2O$); $\delta_H$ (DMSO-d$_6$) 7.08 (1H, dd, J=8.5 and 1.9 Hz, 6-H), 7.20 (1H, d, J, 8-H), 7.99 (1H, d, J=8.5 Hz, 5-H), 8.44 (2H, d, J=6.9 Hz, 2'-H, 6'-H), 8.95 (2H, d, J=6.9 Hz, 3'-H, 5'-H), 10.76 (1H, s, NH); m/z 272 (M+) (Found; m/z 272.0319; $C_{14}H_9ClN_2O_2$ requires 272.0352).

EXAMPLE 65

7-Chloro-2,4-dioxo-3-(2-benzofuranyl)-1,2,3,4-tetrahydroquinoline

This compound was prepared in the same way as described in Example 62, except using benzofuranyl-2-acetic acid (Bisagni et al, Bull. Soc. Chim. Fr., 1962, 86–90), to give the title compound as a white crystalline solid, mpt 342° C.; (Found: C, 65.67; H, 2.96; N, 4.39; $C_{17}H_{10}ClNO_3$ requires C, 65.50; H, 3.23; N, 4.49%); $\delta$(d$_6$DMSO) 11.75 (1H, s, NH), 11.00 (1H, bs, OH), 7.99 (1H, d, J=8.7 Hz, H-5), 7.67 (1H, d, J=8.0 Hz, benzofuran H-6), 7.61 (1H, d, J=8.0 Hz, benzofuran H-5), 7.29 (5H, m, H-6, H-8, benzofuran H-3, H-4, H-7); m/z (EI+) 311 (M+).

EXAMPLE 66

7-Chloro-2,4-dioxo-3-(3-benzofuranyl)-1,2,3,4-tetrahydroquinoline

This compound was prepared in the same way as described in Example 62, except using benzofuranyl-3-acetic acid (Chatterjea et al, J. Indian Chem. Soc., 1980, 633–636), to give the title compound as a white crystalline solid, mpt 290° C. slow decomp; (Found: C, 64.55; H, 3.30; N, 4.49. $C_{17}H_{10}ClNO_3.0.5H_2O$ requires C, 64.55; H, 3.35; N, 4.43%); $\delta$(d$_6$ DMSO) 11.6 (1H, s, NH), 10.58 (1H, bs, OH), 8.1 (1H, s, benzofuran H-2), 7.95 (1H, d, J=8.7 Hz, H-5), 7.62 (1H, d, J=7.4 Hz, benzofuran H-4), 7.34 (2H, m, H-8, benzofuran H-6), 7.23 (2H, m, H-6, benzofuran H-5); m/z (EI+) 311 (M+).

EXAMPLE 67

7-Chloro-2,4-dioxo-3-([3-methyl]-2furanyl)-1,2,3,4-tetrahydroquinoline

To a solution of methyl, 3-methyl furanoate (10 g, 67.6 mmol) in dry tetrahydrofuran (200 ml) under a nitrogen atmosphere at 0° C. was added lithium aluminium hydride (101 ml of a 1M solution in THF, 101 mmol) dropwise over 30 mins. The mixture was heated at reflux for 1 hour, and cooled to room temperature. To this solution was added methanol (70 ml) dropwise, followed by water (3.83 ml), 15% NaOH (3.83 ml), and water (3.83 ml). The mixture was filtered through celite and the solvent was removed under reduced pressure to afford the product (5.43 g) as a pale yellow oil. To a solution of this compound (4.5 g, 40 mmol) in dry dichloromethane (200 ml) under a nitrogen atmosphere was added manganese dioxide (13.98 g, 160 mmol). The mixture was heated to reflux for 1 hour and further manganese dioxide (13.,98 g, 160 mmol) added, and the mixture heated for a further 2 hours. The mixture was cooled to room temperature and filtered through celite. The mixture was washed with saturated sodium hydrogen carbonate (150 ml), saturated sodium chloride (150 ml), dried over $MgSO_4$, filtered and the solvent was removed under reduced pressure to give the product (3.35 g) as a pale yellow oil. To a solution of sodium carbonate (12.9 g, 122 mmol), and potassium cyanide (3.97 g, 61 mmol), in water (150 ml) was added in rapid succession glyoxal bisulphite addition compound (12.12 g, 42.6 mmol), the above product (3.45 g, 30.5 mmol), 1,4-dioxane (7 ml), and water (50 ml). The mixture was stirred at room temperature for 2 hours, then acidified to pH=2 with c.$H_2SO_4$. The mixture was stirred for a further 1 hour then extracted into chloroform (3×100 ml) and the combined organics were extracted with 1N NaOH (200 ml). The aqueous NaOH was washed with chloroform (150 ml), then acidified with c.HCl, and extracted with chloroform (3×100 ml), dried over $MgSO_4$, filtered and the solvent was removed under reduced pressure to give 3-methyl-2-furanacetic acid (2.45 g) as a brown solid.

The title compound was prepared in the same way as described in Example 62 except using 3-methyl-2-furanacetic acid to give the final product as a white crystalline solid, mpt 265° C. slow decomp; (Found: C, 60.50; H, 3.46; N, 4.93. $C_{14}H_{10}ClNO_3.0.2H_2O$ requires C, 60.60; H, 3.70; N, 5.04%); δ($d_6$ DMSO) 11.50 (1H, s, NH), 10.67 (1H, bs, OH), 7.80 (1H, d, J=8.6 Hz, H-5), 7.61 (1H, d, J 1.8 Hz, furan H-5), 7.31 (1H, d, J 2.0 Hz, H-8), 7.21 (1H, dd, J=8.6 and 2.0 Hz, H-6), 6.40 (1H, d, J=1.8 Hz, furan H-4), 1.87 (3H, s, —CH$_3$); m/z (EI+275 (M+).

EXAMPLE 68

7-Chloro-2,4-dioxo-3-(3-(2-methyl)furanyl)-1,2,3,4-tetrahydroquinoline

This compound was prepared in the same way as described in Example 62 except using 2-methylfuranylacetic acid (Heterocycles 23 3 549 1985) to give the title compound as a white crystalline solid; mp 259° C. decomp (from DMF/H$_2$O); δH (DMSO-$d_6$) 2.12 (3H, s, CH$_3$), 6.41 (1H, d, J=1.8 Hz, 4-furanyl-H), 7.16 (1H, dd, J 8.5 Hz and 1.9 Hz, 6-H), 7.30 (1H, d, J=1.9 Hz, 8-H), 7.53 (1H, d, J=1.8 Hz, 5-furanyl-H), 7.89 (1H, d, J=8.5 Hz, 5-H), 10.15 (1H, bs, 3-H), 11.47 (1H, s, NH).

EXAMPLE 69

7-Chloro-2,4-dioxo-3(2-(4-isopropyl)furanyl-1,2,3,4-tetrahydroquinoline

4-Isopropyl-2-furaldehyde (Gilman et al, JACS, 1935, 57 906) was converted to 4-isopropyl furan-2-acetic acid under the conditions of Breen et al, (Aust. J. Chem., 1973, 26, 2221). Reaction of 4-isopropyl furan-2-acetic acid with methyl 2-amino-4-chlorobenzoate under the conditions described in Example 62 gave the title compound as colourless needles; mp 285° C. dec; (Found: C, 62.71; H, 4.51; N, 4.64. $C_{16}H_{14}ClNO_3.0.1H_2O$ requires C, 62.86; H, 4.68; N, 4.58%); δ($d_6$-DMSO, 360 MHz) 1.20 (6H, d, J=6.9 Hz), 2.81 (1H, m), 6.97 (1H, s), 7.23 (1H, dd, J=8.7 and 2.0 Hz), 7.31 (1H, d, J=2.0 Hz), 7.47 (1H, s), 7.93 (1H, d, J=8.7 Hz), 11.65 (1H, br s); m/z (EI) 303 (M+).

EXAMPLE 70

7-Chloro-2,4-dioxo-3(2-(4-methyl)furanyl)-1,2,3,4-tetrahydroquinoline

3-Carboxy-4-methyl-furan-2-acetic acid (13 g) was dissolved in 1,2-dichloromethane (150 ml) with acetyl chloride (20 ml) and heated under reflux for 14 h. After cooling and evaporation, the residue was recrystallised from diethyl ether and collected by filtration to give a solid (9 g), δ(CDCl$_3$, 360 MHz) 2.24 (3H, s), 4.07 (2H, s), 7.28 (1H, s). This was dissolved in ethanol (100 ml) and heated under reflux for 3 h then concentrated in vacuo to give a white solid (9.4 g); δCDCl$_3$ 1.17 (3H, t, J=7.1 Hz), 2.07 (3H, s), 4.0 (2H, s), 4.08 (2H, q, J=7.1 Hz), 7.45 (1H, s), 12.64 (1H, br s). A 4 g portion of this monoester was dissolved in quinoline (30 ml) with cuprous oxide (0.5 g) and heated at 200° C. for 30 minutes. After cooling, the reaction mixture was filtered and diluted with dichloromethane (100 ml), then washed with dilute hydrochloric acid (2×50 ml). The organic layer was dried (Na$_2$SO$_4$), filtered and concentrated under vacuum to give a yellow oil (2.3 g); δ1.25 (3H, t, J=7.1 Hz), 1.99 (3H, s), 3.61 (2H, s), 4.16 (2H, q, J=7.1 Hz), 6.08 (1H, s), 7.11 (1H, s). A 2.1 g portion of the yellow oil was dissolved in 50% aqueous methanol (50 ml) with sodium hydroxide (1 g) and stirred at room temperature for 2 h. After removal of the solvents in vacuo the residue was dissolved in water (50 ml) and washed with diethyl ether (2×30 ml). The aqueous layer was acidified to pH 2 with dilute HCl and extracted into diethyl ether (2×50 ml), dried (Na$_2$SO$_4$), filtered and concentrated in vacuo. The residue was recrystallised from 60-80 petrol to give 4-methyl-furan-2-acetic acid as a colourless solid (1.3 g), δ CDCl$_3$ 1.99 (3H, s), 3.67 (2H, s), 6.11 (1H, s), 7.13 (1H, s). Reaction of 4-methyl-furan-2-acetic acid with methyl-2-amino-4-chlorobenzoate under the conditions described in Example 62 gave the title compound as colourless needles mp 276° C. dec; δ ($d_6$-DMSO, 360 MHz) 2.05 (3H, s), 6.68 (1H, s), 7.23 (1H, dd, J=8.6 and 2.0 Hz), 7.31 (1H, d, J=2.0 Hz), 7.48 (1H, s), 7.93 (1H, d, J=8.6 Hz), 11.64 (1H, br s).

EXAMPLE 71

7-Chloro-2,4-dioxo-3(2-(5-phenyl)furanyl)-1,2,3,4-tetrahydroquinoline

5-Phenyl-2-furaldehyde (kaltenbronn et al, J. Med. Chem., 1968, 902) was converted to 5-phenylfuran-2-acetic acid under the conditions of Breen et al, (Aust. J. Chem., 1973, 26, 2221). Reaction of 5-phenyl-furan-2-acetic acid with methyl 2-amino-4-chlorobenzoate under the conditions described in Example 62 gave the title compound as colourless needles mp>300° C.; (Found: C, 66.69; H, 3.56; N, 4.08. $C_{19}H_{12}ClNO_3$ requires C, 66.50; H, 3.70; N, 4.08%; δ ($d_6$-DMSO, 360 MHz) 7.06 (2H, s), 7.24-7.46 (5H, m), 7.76 (2H, d, J=7.4 Hz), 8.00 (1H, d, J=8.7 Hz), 10.80 (1H, br s), 11.66 (1H, br, s); m/z (EI) 337 (M+).

EXAMPLE 72

7-Chloro-2,4-dioxo-3-(2-(5-methyl)thienyl)-1,2,3,4-tetrahydroquinoline

This compound was prepared in the same way as described in Example 60 except using 5-methyl-thienylacetic acid to give the title compound as a white crystalline solid; mp 285° C. slow decomp. (MeOH, DMF, H$_2$O) (Found: C, 57.68; H, 3.71; N, 4.58; $C_{14}H_{10}ClNO_2S$ requires C, 57.64; H, 3.46; N, 4.80%); δH (DMSO-$d_6$) 2.46 (3H, s, CH$_3$), 6.78 (1H, d, J=3.7 Hz, 4-thienyl-H), 7.24 (1H, dd, J=8.5 Hz and 1.9 Hz, 6-H), 7.33 (1H, d, J=1.9 Hz, 8-H), 7.84 (1H, d, J=3.7 Hz, 3-thienyl-H), 8.04 (1H, d, J=8.5 Hz, 5-H), 11.15 (1H, bs, 3-H), 11.72 (1H, s, NH); m/z 292 (M+1).

EXAMPLE 73

3-(2-(5-Benzyl)thienyl)-7-chloro-2,4-dioxo-1,2,3,4-tetrahydroquinoline

This compound was prepared in the same way as described in Example 60 except using 5-benzylthienylacetic acid to give the title compound as a white crystalline solid; mp 195° C. slow decomp. (DMF, H$_2$O) (Found: C, 63.48; H, 3.56; N, 3.77; $C_{20}H_{14}ClNO_2S.0.92H_2O$ requires C, 63.86; H, 4.00; N, 3.72%) δH (DMSO-$d_6$) 4.14 (2H, s, CH$_2$), 6.86 (1H, d, J=3.8 Hz, 3-thienyl-H), 7.19-7.34 (7H, m, 8-H, 5-H, Ar), 7.89 (1H, d, J=3.8 Hz, 4-thienyl-H), 8.04 (1H, d, J=8.5 Hz, 5-H), 11.24 (1H, bs, 3-H), 11.74 (1H, s, NH); m/z 368 (M+1).

EXAMPLE 74

3-(3-Benzothienyl)-7-chloro-2,4-dioxo-1,2,3,4-tetrahydroquinoline

To a solution of methyl-4-chloroanthranilate (1 g, 5.4 mmol) and methyl benzothienyl-2-acetate (1.3 g, 5.94 mmol) in dry tetrahydrofuran (50 ml) was added a solution of potassium hexamethyldisilazide in toluene (0.5M, 26 ml, 12.5 mmol) and the reaction stirred for 2 h. Methanol (15 ml) was added and the solvent evaporated. The residue was partitioned between aqueous sodium hydroxide (1M, 40 ml) and diethyl ether (40 ml), and the aqueous layer was acidified with hydrochloric acid (5M). The resultant precipitate was collected and recrystallised from dimethylformamide/water to afford the title compound as a white solid; mp 320° C. slow decomp. (from DMF/H$_2$O) (Found: C, 61.65; H, 2.86; N, 4.08; C$_{17}$H$_{10}$ClNO$_2$S.0.1H$_2$O requires C, 61.95; H, 3.12; N, 4.25) δH (DMSO-d$_6$) 7.22 (1H, dd, J=8.5 Hz and 1.9 Hz, 6-H), 7.34–7.41 (4H, m, 8-H, Ar), 7.87 (1H, s, 2-thienyl-H), 7.94 (1H, d, J=8.5 Hz, 7-thienyl-H), 8.01 (1H, d, J=8.5 Hz, 5-H), 10.4 (1H, bs, 3-H), 11.59 (1H, s, NH); m/z 328 (M+1).

TABLET PREPARATION

Tablets containing 1.0, 2.0, 25.0, 26.0, 50.0 and 100.0 mg, respectively of the following compounds are prepared as illustrated below:

3-(Cyclopropanecarbonyl)-7-chloro-2,4-dioxo-1,2,3,4-tetrahydroquinoline 3-(5'-[2'-Methylfuranyl])-7-chloro-2,4-dioxo-1,2,3,4-tetrahydroquinoline Methyl 7-Chloro-2,4-dioxo-3-(1,2,3,4-tetrahydroquinoline)carboxylate (E)-(3-Methoxyphenyl)prop-2-enyl 7-Chloro-2,4-dioxo-3-(1,2,3,4-tetrahydroquinoline)carboxylate 7-Chloro-2,4-dioxo-3-(3-pyridyl)-1,2,3,4-tetrahydroquinoline.

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

What is claimed is:

1. A compound represented by formula IIA:

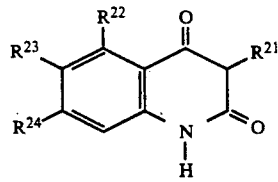

and pharmaceutically acceptable salts thereof, wherein
R$^{21}$ represents —COR$^{26}$ or —CO$_2$R$^{26}$;
R$^{23}$ is hydrogen;
R$^{22}$, and R$^{24}$ are independently selected from the group consisting of hydrogen, halogen, cyano, trifluoromethyl, nitro, hydroxy, amino, carboxy, C$_{1-6}$ alkyl, C$_{1-6}$ alkoxy, C$_{1-6}$ alkylthio and C$_{2-6}$ alkoxycarbonyl, provided that at least one of R$^{22}$, and R$^{24}$ is other than hydrogen, and R$^{26}$ is selected from the group consisting of C$_{3-7}$ cycloalkyl, aryl (C$_{1-6}$)alkyl, aryl (C$_{2-6}$)alkenyl, aryl(C$_{2-6}$)alkynyl, heteroaryl(C$_{1-6}$)alkyl, selected from the group consisting of indolyethyl, indolylpropyl or thienylethyl, and heteroaryl (C$_{2-6}$)alkenyl selected from thienylvinyl, any of which groups can be substituted by hydroxy, C$_{1-6}$ alkoxy, C$_{1-6}$ alkoxy (C$_{1-6}$) alkoxy and C$_{2-6}$ alkoxycarbonylamino (C$_{1-6}$)-alkyl and wherein said aryl group is selected from phenyl and naphthyl.

2. A compound represented by formula IIB:

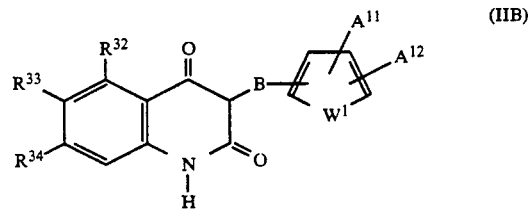

and pharmaceutically acceptable salts thereof, wherein
W$^1$ represents oxygen, sulphur or N—A$^{13}$;
A$^{11}$ and A$^{12}$ are independently selected from the group consisting of hydrogen, halogen, cyano, trifluoromethyl, nitro, hydroxy, amino, carboxy, C$_{1-6}$ alkyl, C$_{2-6}$ alkenyl, C$_{2-6}$ alkynyl, C$_{3-7}$ cycloalkyl, C$_{3-7}$ cycloalkyl (C$_{1-6}$)alkyl, C$_{3-7}$ cycloalkyl(C$_{1-6}$)alkyl, aryl, aryl (C$_{1-6}$)alkyl, C$_{1-6}$ alkoxy, C$_{2-6}$ alkenyloxy, C$_{1-6}$ alkylthio, C$_{2-6}$ alkenylthio, C$_{2-6}$ alkylcarbonyl, arylcarbonyl and C$_{2-6}$ alkoxycarbonyl; or A$^{11}$ and A$^{12}$ together represent a fused benzo ring, which can be substituted by nitro or C$_1$-C$_6$ alkoxy;
A$^{13}$ is selected from the group consisting of hydrogen, C$_{1-6}$ alkyl and aryl (C$_{1-6}$) alkyl;
B represents a bond or a carbonyl group (C=O); and
R$^{33}$ is hydrogen
R$^{32}$, and R$^{34}$ are independently selected from the group consisting of hydrogen, halogen, cyano, trifluoromethyl, nitro, hydroxy, amino, carboxy, C$_{1-6}$ alkyl, C$_{1-6}$ alkoxy, C$_{1-6}$ alkylthio and C$_{2-6}$ alkoxycarbonyl, provided that at least one of R$^{32}$, and R$^{34}$ is other than hydrogen and wherein aryl is selected from phenyl or naphthyl.

3. A compound represented by formula IIC:

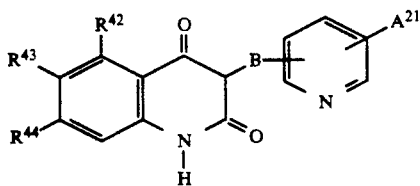

(IIC)

and pharmaceutically acceptable salts thereof, wherein
A$^{21}$ is selected from the group consisting of hydrogen, halogen, cyano, trifluoromethyl, nitro, hydroxy, amino, carboxy, C$_{1-6}$ alkyl, C$_{1-6}$ alkoxy, C$_{1-6}$ alkylthio, C$_{2-6}$ alkylcarbonyl, arylcarbonyl and C$_{2-6}$ alkoxycarbonyl;

B represents a bond or a carbonyl group (C=O); and R$^{43}$ is hydrogen,

R$^{42}$, and R$^{44}$ are independently selected from the group consisting of hydrogen, halogen, cyano, trifluoromethyl, nitro, hydroxy, amino, carboxy, C$_{1-6}$ alkyl, C$_{1-6}$ alkoxy, C$_{1-6}$ alkylthio and C$_{2-6}$ alkoxycarbonyl, provided that at least one of R$^{42}$, and R$^{44}$ is other than hydrogen.

4. A compound selected from the group consisting of:
3-benzyloxycarbonyl-7-chloro-2,4-dioxo-1,2,3,4-tetrahydroquinoline;
7-chloro-2,4-dioxo-3-(2-phenylethoxy)carbonyl-1,2,3,4-tetrahydroquinoline;
7-chloro-2,4-dioxo-3-(3-phenylpropoxy)carbonyl-1,2,3,4-tetrahydroquinoline;
7-chloro-2,4-dioxo-3-[2-(3-hydroxyphenyl)ethoxy]carbonyl-1,2,3,4-tetrahydroquinoline;
7-chloro-2,4-dioxo-3-[3-(4-hydroxyphenyl)propoxy]carbonyl-1,2,3,4-tetrahydroquinoline;
7-chloro-2,4-dioxo-3-[2-(2-hydroxyphenyl)ethoxy]carbonyl-1,2,3,4-tetrahydroquinoline;
7-chloro-3-cyclopropylmethoxycarbonyl-2,4-dioxo-1,2,3,4-tetrahydroquinoline;
7-chloro-2,4-dioxo-3-[2-(4-hydroxyphenyl)ethoxy]carbonyl-1,2,3,4-tetrahydroquinoline;
7-chloro-2,4-dioxo-3-(3-hydroxyphenylmethoxy)carbonyl-1,2,3,4-tetrahydroquinoline;
7-chloro-2,4-dioxo-3-(pyrid-2-ylmethoxy)carbonyl-1,2,3,4-tetrahydroquinoline;
2,4-dioxo-3-[3-(4-hydroxyphenyl)propoxy]carbonyl-7-nitro-1,2,3,4-tetrahydroquinoline;
7-chloro-2,4-dioxo-3-(2-hydroxyethoxy)carbonyl-1,2,3,4-tetrahydroquinoline;
7-chloro-2,4-dioxo-3-(3-thienyl)carbonyl-1,2,3,4-tetrahydroquinoline;
7-chloro-2,4-dioxo-3-(2-furyl)carbonyl-1,2,3,4-tetrahydroquinoline;
7-chloro-2,4-dioxo-3-(2-thienyl)carbonyl-1,2,3,4-tetrahydroquinoline;
7-chloro-3-(2,5-dimethyl-3-furyl)carbonyl-2,4-dioxo-1,2,3,4-tetrahydroquinoline;
7-chloro-2,4-dioxo-3-(5-methyl-2-furyl)carbonyl-1,2,3,4-tetrahydroquinoline;
7-chloro-2,4-dioxo-3-[2-(5-nitrobenzofuryl)carbonyl]-1,2,3,4-tetrahydroquinoline;
3-[2-(benzofuryl)carbonyl]-7-chloro-2,4-dioxo-1,2,3,4-tetrahydroquinoline;
3-[2-(benzo[b]thienyl)carbonyl]-7-chloro-2,4-dioxo-1,2,3,4-tetrahydroquinoline;
3-benzylcarbonyl-7-chloro-2,4-dioxo-1,2,3,4-tetrahydroquinoline;
7-chloro-2,4-dioxo-3-(5-methyl-2-thienyl)carbonyl-1,2,3,4-tetrahydroquinoline;
7-chloro-2,4-dioxo-3-(3-methyl-2-thienyl)carbonyl-1,2,3,4-tetrahydroquinoline;
7-chloro-3-(2,5-dimethyl-3-thienyl)carbonyl-2,4-dioxo-1,2,3,4-tetrahydroquinoline;
7-chloro-2,4-dioxo-3-[2-(3-thienyl)ethenyl]carbonyl-1,2,3,4-tetrahydroquinoline;
3-(5-bromo-2-thienyl)carbonyl-7-chloro-2,4-dioxo-1,2,3,4-tetrahydroquinoline;
7-chloro-2,4-dioxo-3-(1-methylpyrrol-2-yl)carbonyl-1,2,3,4-tetrahydroquinoline;
7-chloro-2,4-dioxo-3-(1-methylpyrrol-3-yl)carbonyl-1,2,3,4-tetrahydroquinoline;
7-chloro-2,4-dioxo-3-(1-methylindol-3-yl)carbonyl-1,2,3,4-tetrahydroquinoline;
7-chloro-3-cyclopropylcarbonyl-2,4-dioxo-1,2,3,4-tetrahydroquinoline;
7-chloro-2,4-dioxo-3-(5-methyl-2-furyl)-1,2,3,4-tetrahydroquinoline;
7-chloro-2,4-dioxo-3-(5-ethyl-2-furyl)-1,2,3,4-tetrahydroquinoline;
7-chloro-2,4-dioxo-3-(1-methylpyrrol-2-yl)-1,2,3,4-tetrahydroquinoline;
7-chloro-2,4-dioxo-3-(2-furyl)-1,2,3,4-tetrahydroquinoline;
3-(4-benzoyl-1-methylpyrrol-2-yl)-7-chloro-2,4-dioxo-1,2,3,4-tetrahydroquinoline;
3-(5-benzoyl-1-methylpyrrol-2-yl)-7-chloro-2,4-dioxo-1,2,3,4-tetrahydroquinoline;
7-chloro-2,4-dioxo-3-[2-(5-methoxyindol-3-yl)ethoxy]carbonyl-1,2,3,4-tetrahydroquinoline;
7-chloro-2,4-dioxo-3-[3-(3-methoxyphenyl)prop-2-ynyloxy]carbonyl-1,2,3,4-tetrahydroquinoline;
7-chloro-2,4-dioxo-3-(3-indol-3-ylpropoxy)carbonyl-1,2,3,4-tetrahydroquinoline;
3-[2-[3,4-bis(methoxymethoxy)phenyl]ethoxy]carbonyl-7-chloro-2,4-dioxo-1,2,3,4-tetrahydroquinoline;
7-chloro-2,4-dioxo-3-[4-(3-hydroxyphenyl)butoxy]carbonyl-1,2,3,4-tetrahydroquinoline;
7-chloro-2,4-dioxo-3-[3-(3-hydroxyphenyl)propoxy]carbonyl-1,2,3,4-tetrahydroquinoline;
7-chloro-2,4-dioxo-3-(2-indol-3-ylethoxy)carbonyl-1,2,3,4-tetrahydroquinoline;
7-chloro-2,4-dioxo-3-[3-(2-hydroxyphenyl)propoxy]carbonyl-1,2,3,4-tetrahydroquinoline;
3-[2-[4-(N-t-butoxycarbonylaminomethyl)phenyl]ethoxy]carbonyl-7-chloro-2,4-dioxo-1,2,3,4-tetrahydroquinoline;
7-chloro-2,4-dioxo-3-[2-(3-thienyl)ethoxy]carbonyl-1,2,3,4-tetrahydroquinoline;
7-chloro-2,4-dioxo-3-[2-(2-thienyl)ethoxy]carbonyl-1,2,3,4-tetrahydroquinoline;
7-chloro-2,4-dioxo-3-[3-(3-hydroxyphenyl)prop-2-ynyloxy]carbonyl-1,2,3,4-tetrahydroquinoline;
7-chloro-2,4-dioxo-3-[3-(3-methoxyphenyl)prop-2-enyloxy]carbonyl-1,2,3,4-tetrahydroquinoline;
7-chloro-2,4-dioxo-3-[2-(phenylthio)ethoxy]carbonyl-1,2,3,4-tetrahydroquinoline;
7-chloro-2,4-dioxo-3-[2-(phenyl)ethylthio]carbonyl-1,2,3,4-tetrahydroquinoline;
7-chloro-2,4-dioxo-3-(2-indol-3-ylethoxy)carbonyl-5-iodo-1,2,3,4-tetrahydroquinoline;
7-chloro-2,4-dioxo-3-(3-methyl-1,2,4-oxadiazol-5-yl)1,2,3,4-tetrahydroquinoline;
7-chloro-2,4-dioxo-3-[2-(ethoxycarbonyl)ethenyl]-1,2,3,4-tetrahydroquinoline;

7-chloro-2,4-dioxo-1,2,3,4-tetrahydroquinoline-3-hydroxamic acid;
7-chloro-2,4-dioxo-5-iodo-1,2,3,4-tetrahydroquinoline-3-hydroxamic acid;
7-chloro-2,4-dioxo-1,2,3,4-tetrahydroquinoline-3-carboxylic acid hydrazide;
7-chloro-2,4-dioxo-3-(3-thienyl)-1,2,3,4-tetrahydroquinoline;
7-chloro-2,4-dioxo-3-(2-thienyl)-1,2,3,4-tetrahydroquinoline;
7-chloro-2,4-dioxo-3-(2-pyridyl)-1,2,3,4-tetrahydroquinoline;
7-chloro-2,4-dioxo-3-(3-pyridyl)-1,2,3,4-tetrahydroquinoline;
7-chloro-2,4-dioxo-3-(4-pyridyl)-1,2,3,4-tetrahydroquinoline;
3-(2-benzofuryl)-7-chloro-2,4-dioxo-1,2,3,4-tetrahydroquinoline;
3-(3-benzofuryl)-7-chloro-2,4-dioxo-1,2,3,4-tetrahydroquinoline;
7-chloro-2,4-dioxo-3-(3-methyl-2-furyl)-1,2,3,4-tetrahydroquinoline;
7-chloro-2,4-dioxo-3-(2-methyl-3-furyl)-1,2,3,4-tetrahydroquinoline;
7-chloro-2,4-dioxo-3-(4-isopropyl-2-furyl)-1,2,3,4-tetrahydroquinoline;
7-chloro-2,4-dioxo-3-(4-methyl-2-furyl)-1,2,3,4-tetrahydroquinoline;
7-chloro-2,4-dioxo-3-(5-phenyl-2-furyl)-1,2,3,4-tetrahydroquinoline;
7-chloro-2,4-dioxo-3-(5-methyl-2-thienyl)-1,2,3,4-tetrahydroquinoline;
3-(5-benzyl-2-thienyl)-7-chloro-2,4-dioxo-1,2,3,4-tetrahydroquinoline;
3-(3-benzo[b]thienyl)-7-chloro-2,4-dioxo-1,2,3,4-tetrahydroquinoline;
and pharmaceutically acceptable salts thereof.

5. A compound selected from:
2,4-dioxo-3-ethoxycarbonyl-6-nitro-1,2,3,4-tetrahydroquinoline;
7-chloro-2,4-dioxo-3-methoxycarbonyl-1,2,3,4-tetrahydroquinoline;
7-chloro-2,4-dioxo-3-n-propoxycarbonyl-1,2,3,4-tetrahydroquinoline;
6,7-dinitro-2,4-dioxo-3-ethoxycarbonyl-1,2,3,4-tetrahydroquinoline;
7-chloro-2,4-dioxo-3-ethoxycarbonyl-1,2,3,4-tetrahydroquinoline;
2,4-dioxo-3-ethoxycarbonyl-7-nitro-1,2,3,4-tetrahydroquinoline;
7-chloro-2,4-dioxo-3-n-pentyloxycarbonyl-1,2,3,4-tetrahydroquinoline;
7-chloro-2,4-dioxo-3-ethoxycarbonyl-5-iodo-1,2,3,4-tetrahydroquinoline;
7-chloro-2,4-dioxo-5-ethyl-3-methoxycarbonyl-1,2,3,4-tetrahydroquinoline;
3-carboxy-7-chloro-2,4-dioxo-1,2,3,4-tetrahydroquinoline; and pharmaceutically acceptable salts.

6. A pharmaceutical composition comprising an effective amount of at least one compound according to claim 4 or a pharmaceutically acceptable salt thereof in association with one or more pharmaceutically acceptable carriers and/or excipients.

7. A pharmaceutical composition comprising an effective amount of at least one compound according to claim 5 or a pharmaceutically acceptable salt thereof in association with one or more pharmaceutically acceptable carriers and/or excipients.

8. A pharmaceutical composition comprising an effective amount of at least one compound according to claim 1 or a pharmaceutically acceptable salt thereof in association with one or more pharmaceutically acceptable carriers and/or excipients.

9. A pharmaceutical composition comprising an effective amount of at least one compound according to claim 2 or a pharmaceutically acceptable salt thereof in association with one or more pharmaceutically acceptable carriers and/or excipients.

10. A pharmaceutical comprising an effective amount of at least one compound according to claim 3 or a pharmaceutically acceptable salt thereof in association with one or more pharmaceutically acceptable carriers and/or excipients.

* * * * *